(12) United States Patent
Bhatia et al.

(10) Patent No.: US 9,279,005 B2
(45) Date of Patent: Mar. 8, 2016

(54) FUSION PROTEINS AND THEIR USE IN THE DIAGNOSIS AND TREATMENT OF LEISHMANIASIS

(71) Applicant: Infectious Disease Research Institute, Seattle, WA (US)

(72) Inventors: Ajay Bhatia, Seattle, WA (US); Steven G. Reed, Seattle, WA (US)

(73) Assignee: Infectious Disease Research Institute, Seattle, WA (US)

( * ) Notice: Subject to any disclaimer, the term of this patent is extended or adjusted under 35 U.S.C. 154(b) by 0 days.

(21) Appl. No.: 14/286,647

(22) Filed: May 23, 2014

(65) Prior Publication Data

US 2015/0017200 A1    Jan. 15, 2015

Related U.S. Application Data

(63) Continuation of application No. 13/560,565, filed on Jul. 27, 2012, now Pat. No. 8,771,710, which is a continuation of application No. 12/497,178, filed on Jul. 2, 2009, now Pat. No. 8,231,881.

(60) Provisional application No. 61/078,255, filed on Jul. 3, 2008.

(51) Int. Cl.
| | |
|---|---|
| G01N 33/569 | (2006.01) |
| C12P 21/04 | (2006.01) |
| A61K 39/008 | (2006.01) |
| C07K 14/44 | (2006.01) |
| G01N 33/68 | (2006.01) |
| C07K 16/20 | (2006.01) |
| A61K 38/00 | (2006.01) |
| A61K 39/00 | (2006.01) |

(52) U.S. Cl.
CPC .............. *C07K 14/44* (2013.01); *C07K 16/20* (2013.01); *G01N 33/56905* (2013.01); *G01N 33/6893* (2013.01); *A61K 38/00* (2013.01); *A61K 39/00* (2013.01); *Y10S 435/81* (2013.01); *Y10S 435/975* (2013.01)

(58) Field of Classification Search
CPC ....... A61K 38/00; A61K 39/00; C07K 14/44; C07K 16/20; G01N 33/56905; G01N 33/6893
See application file for complete search history.

(56) References Cited

U.S. PATENT DOCUMENTS

| | | | |
|---|---|---|---|
| 4,992,273 A | 2/1991 | Monjour et al. | |
| 5,304,371 A | 4/1994 | Reed | |
| 5,411,865 A | 5/1995 | Reed | |
| 5,571,515 A | 11/1996 | Scott et al. | |
| 5,719,263 A | 2/1998 | Reed | |
| 5,733,778 A | 3/1998 | Matlashewski et al. | |
| 5,744,593 A | 4/1998 | Klimowski et al. | |
| 5,756,662 A | 5/1998 | Reed | |
| 5,834,592 A | 11/1998 | Reed et al. | |
| 5,846,748 A | 12/1998 | Mandal et al. | |
| 5,876,735 A | 3/1999 | Reed | |
| 5,876,966 A | 3/1999 | Reed | |
| 5,879,687 A | 3/1999 | Reed | |
| 5,910,306 A | 6/1999 | Alving et al. | |
| 5,912,166 A | 6/1999 | Reed et al. | |
| 5,961,970 A | 10/1999 | Lowell et al. | |
| 5,965,142 A | 10/1999 | Dillon et al. | |
| 5,980,898 A | 11/1999 | Glenn et al. | |
| 5,985,284 A | 11/1999 | Lowell | |
| 6,013,268 A | 1/2000 | Reed | |
| 6,031,077 A | 2/2000 | Klimowski et al. | |
| 6,054,135 A | 4/2000 | Reed et al. | |
| 6,228,372 B1 | 5/2001 | Reed et al. | |
| 6,365,165 B1 | 4/2002 | Reed et al. | |
| 6,375,955 B1 | 4/2002 | Reed et al. | |
| 6,500,437 B1 | 12/2002 | Reed et al. | |
| 6,607,731 B1 | 8/2003 | Reed et al. | |
| 6,613,337 B1 | 9/2003 | Reed et al. | |
| 6,638,517 B2 | 10/2003 | Reed et al. | |
| 6,660,840 B1 | 12/2003 | Reed | |
| 6,709,661 B1 | 3/2004 | Reed et al. | |
| 7,189,522 B2 | 3/2007 | Esfandiari | |
| 7,833,534 B2 | 11/2010 | Goto et al. | |
| 8,231,881 B2 | 7/2012 | Bhatia et al. | |
| 8,410,258 B2 | 4/2013 | Goto et al. | |
| 8,771,710 B2 | 7/2014 | Bhatia et al. | |
| 8,865,180 B2 | 10/2014 | Goto et al. | |
| 2002/0081320 A1 | 6/2002 | Reed et al. | |
| 2009/0041798 A1 | 2/2009 | Reed et al. | |

(Continued)

FOREIGN PATENT DOCUMENTS

| | | |
|---|---|---|
| EP | 0 293 827 A2 | 12/1988 |
| EP | 0 293 827 A3 | 12/1988 |

(Continued)

OTHER PUBLICATIONS

Afonso, L.C.C. et al. (Jan. 14, 1994). "The Adjuvant Effect of Interleukin-12 in a Vaccine Against Leishmania major," *Science* 263:235-237.

Attar, Z.J. et al. (2001). "Latex Agglutination Test for the Detection of Urinary Antigens in Visceral Leishmaniasis," *Acta Tropica* 78:11-16.

Benson, G. (1999). "Tandem Repeats Finder: A Program to Analyze DNA Sequences," *Nucleic Acids Research* 27(2):573-580.

Berman, J.D. (1997). "Human Leishmaniasis: Clinical, Diagnostic, and Chemotherapeutic Developments in the Last 10 Years," *Clinical Infectious Diseases* 24:684-703.

(Continued)

*Primary Examiner* — Padma V Baskar
(74) *Attorney, Agent, or Firm* — Morrison & Foerster LLP

(57) ABSTRACT

The present invention relates generally to a fusion protein made from a synthetic gene construct comprising of elements derived from the *Leishmania* antigens K26, K39, and K9. The fusion protein is particularly useful in the diagnosis of leishmaniasis, particularly visceral leishmaniasis in animals such as humans and dogs.

10 Claims, 3 Drawing Sheets

(56) References Cited

U.S. PATENT DOCUMENTS

| | | |
|---|---|---|
| 2009/0291099 A1 | 11/2009 | Goto et al. |
| 2010/0008924 A1 | 1/2010 | Bhatia et al. |
| 2012/0114688 A1 | 5/2012 | Bhatia et al. |
| 2013/0071862 A1 | 3/2013 | Bhatia et al. |

FOREIGN PATENT DOCUMENTS

| | | |
|---|---|---|
| EP | 0 679 259 B1 | 3/1999 |
| WO | WO-89/01045 A1 | 2/1989 |
| WO | WO-93/16199 A1 | 8/1993 |
| WO | WO-94/016331 A1 | 7/1994 |
| WO | WO-95/29239 A2 | 11/1995 |
| WO | WO-95/29239 A3 | 11/1995 |
| WO | WO-96/33414 A2 | 10/1996 |
| WO | WO-96/33414 A3 | 10/1996 |
| WO | WO-96/39524 A1 | 12/1996 |
| WO | WO-97/011180 A1 | 3/1997 |
| WO | WO-98/35045 A2 | 8/1998 |
| WO | WO-98/35045 A3 | 8/1998 |
| WO | WO-2007/121184 A2 | 10/2007 |
| WO | WO-2007/121184 A3 | 10/2007 |
| WO | WO-2007/121184 A9 | 10/2007 |
| WO | WO-2009/012166 A1 | 1/2009 |
| WO | WO-2009/143006 A1 | 11/2009 |
| WO | WO-2010/003085 | 1/2010 |
| WO | WO-2012/064659 A1 | 5/2012 |
| WO | WO-2014/160985 A2 | 10/2014 |
| WO | WO-2014/160987 A2 | 10/2014 |

OTHER PUBLICATIONS

Bixler, G.S. Jr. et al. (1987). "B Cell Recognition of Protein Antigens—PERSPF from the Submolecular Level," Chapter 4 in Synthetic Vaccines vol. I, Arnon, R. ed., CRC Press, Inc., Boca Raton, Florida, pp. 39-71.

Blaxter, M.L. et al. (1988). "Specific Serodiagnosis of Visceral Leishmaniasis Using a Leishmania donovani Antigen Identified by Expression Cloning," Molecular Biochemical Parasitology 30:259-270.

Boarino, A. et al. (May 2005). "Development of Recombinant Chimeric Antigen Expressing Immunodominant B Epitopes of *Leishmania infantum* for Serodiagnosis of Visceral Leishmaniasis," *Clinical and Diagnostic Laboratory Immunology* 12(5):647-653.

Bowie, J.U. et al. (Mar. 16, 1990). "Deciphering the Message in Protein Sequences: Tolerance to Amino Acid Substitutions," Science 247:1306-1310.

Bunn-Moreno, M.M. et al. (Aug. 1981). "Lectin(s) Extracted from Seeds of Artocarpus Integrifolia (Jackfruit): Potent and Selective Stimulator(s) of Distinct Human T and B Cell Functions," The Journal of Immunology 127(2):427-429.

Burns, J.M. Jr. et al. (Feb. 1992). "Identification and Synthesis of a Major Conserved Antigenic Epitope of Trypanosoma cruzi," Proc. Natl. Acad. Sci. USA 89:1239-1243.

Burns, J.M. Jr. et al. (Jan. 15, 1993). "Molecular Characterization of a Kinesin-Related Antigen of Leishmania chagasi that Detects Specific Antibody in African and American Visceral Leishmaniasis," Proc. Natl. Acad. Sci. USA, 90(2):775-779.

Campos-Neto, A. et al. (Nov. 1995). "Cloning and Expression of a Leishmania donovani Gene Instructed by a Peptide Isolated from Major Histocompatibility Complex Class II Molecules of Infected Macrophages," Journal of Experimental Medicine 182(5):1423-1433.

Champsi, J. et al. (Dec. 1988). "Membrane Glycoprotein M-2 Protects Against Leishmania amazonensis Infection," Infection and Immunity 52(12):3272-3279.

Chatelain, R. et al. (Feb. 15, 1992). "IL-4 Induces a Th2 Response in Leishmania major-Infected Mice," The Journal of Immunology 148(4):1182-1187.

Cornelissen, A.W.C.A. et al. (Sep. 1996). "Vaccines Against Protozoal Diseases of Veterinary Importance," FEMS Immunology and Medical Microbiology 15:61-72.

Coulson, R.M.R. et al. (Nov. 1996). "Differential Expression of Leishmania major β-Tubulin Genes During the Acquisition of Promastigote Infectivity," Molecular and Biochemical Parasitology 82(2):227-236.

Curry, R.C. et al. (1987). "A Sensitive Immunochemical Assay for Biologically Active MuIFN-γ," Journal of Immunological Methods 104:137-142.

Dapra, F. et al. (2008). "Validation of a Recombinant Based Antibody ELISA for Diagnosis of Human and Canine Leishmaniasis," Journal of Immunoassay and Immunochemistry 29:244-256.

De Andrade, C.R. et al. (Feb. 1992). "Recombinant Leishmania Hsp90 and Hsp70 are Recognized by Sera from Visceral Leishmaniasis Patients but Not Chagas' Disease Patients," Journal of Clinical Microbiology 30(2):330-335.

De Groot, A.S. et al. (2001). "From Genome to Vaccine: in Silico Predictions, Ex Vivo Verification," Vaccine 19:4385-4395.

Dillon, D.C. et al. (Aug. 1995). "Characterization of a Leishmania tropica Antigen that Detects Immune Responses in Desert Storm Viscerotropic Leishmaniasis Patients," Proc. Natl. Acad. Sci. USA 92:7981-7985.

Flinn, H.M. et al. (1994). "Expression of a Hydrophilic Surface Protein in Infective Stages of Leishmania major," Molecular and Biochemical Parasitology 65:259-270.

Fong, D. (Oct. 1988). "Beta Tubulin Gene of the Parasitic Protozoan Leishmania mexicana," Molecular and Biochemical Parasitology 31(1):97-106.

Frommel, D. et al. (Apr. 1988). "Vaccine-Induced Immunity Against Cutaneous Leishmaniasis in BALB/c Mice," Infection and Immunity 56(4):843-848.

GenBank Accession No. FR796397, last updated Dec. 16, 2011, located at http://www.ncbi.nlm.nih.gov/nuccore/FR796397, last visited on Aug. 30, 2013, 83 pages.

GenBank Accession No. U73845, last updated Oct. 18, 2002, located at http://www.ncbi.nlm.nih.gov/nuccore/U73845, last visited on Aug. 30, 2013, two pages.

GenBank Accession No. U19888, last updated Oct. 31, 1995, located at http://www.ncbi.nlm.nih.gov/nuccore/U19888, last visited on Aug. 30, 2013, two pages.

GenBank Accession No. X86551, last updated Jan. 25, 1996, located at http://www.ncbi.nlm.nih.gov/nuccore/X86551, last visited on Aug. 30, 2013, one page.

Goto, Y. et al. (Feb. 2007, e-pub. Nov. 6, 2006). "Bioinformatic Identification of Tandem Repeat Antigens of the Leishmania donovani Complex," Infection and Immunity 75(2):846-851.

Houghten, R.A et al. (1986). "Relative Importance of Position and Individual Amino Acid Residues in Peptide Antigen-Antibody Interactions: Implications in the Mechanism of Antigenic Drift and Antigenic Shift," in Vaccines 86. New Approaches to Immunization. Developing Vaccines Against Parasitic, Bacterial, and Viral Diseases, Brown, F. et al. (eds.), Cold Spring Harbor Laboratory, pp. 21-25.

Jaffe, C.L. et al. (1988). "Purification of Two Leishmania donovani Membrane Proteins Recognized by Sera from Patients with Visceral Leishmaniasis," Molecular and Biochemical Parasitology 27:53-62.

Jeronimo, S.M.B. et al. (1994). "An Urban Outbreak of Visceral Leishmaniasis in Natal Brazil," Transactions of the Royal Societyof Tropical Medicine and Hygiene 88:386-388.

Lederman, S. et al. (1991). "A Single Amino Acid Substitution in a Common African Allele of the CD4 Molecule Ablates Binding of the Monoclonal Antibody, OKT4," *Molecular Immunology* 28(11):1171-1181.

Levinson, W.E. et al. (1994). "Immunity" Chapter 57 in Medical Microbiology & Immunology, 3rd Edition, Appleton & Lange, East Norwalk, CT, pp. 292-293.

Li, C.H. et al. (Jun. 1980). "β-Endorphin Omission Analogs: Dissociation of Immunoreactivity from other Biological Activities," *Proc. Natl. Acad. Sci. USA* 77(6):3211-3214.

Magill, A.J. et al. (May 13, 1993). "Visceral Infection Caused by Leishmania Tropica in Veterans of Operation Desert Storm," The New England Journal of Medicine 328(19):1383-1387.

Miller, R.A. et al. (1990). "Leishmania gp63 Molecule Implicated in Cellular Adhesion Lacks an Arg-Gly-Asp Sequence," Molecular and Biochemical Parasitology 39:267-274.

(56) References Cited

OTHER PUBLICATIONS

Mosmann, T.R. et al. (1989). "Specific Assay for Cytokine Production by T Cells," Journal of Immunological Methods 116:151-158.

Mougneau, E. et al. (Apr. 28, 1995). "Expression Cloning of a Protective Leishmania Antigen," Science 268:563-566.

Nascimento, E. et al. (Jul. 1990). "Vaccination of Humans Against Cutaneous Leishmaniasis: Cellular and Humoral Immune Responses," Infection and Immunity 58(7):2198-2203.

Osland, A. et al. (Apr. 1992). "Isolation and Characterization of Recombinant Antigens from Leishmania aethiopica that React with Human Antibodies," Infection and Immunity 60(4):1368-1374.

Pan, A.A. et al. (Mar.-Apr. 1993). "Developmental Life Cycle of Leishmania—Cultivation and Characterization of Cultured Extracellular Amastigotes," The Journal of Eukaryotic Microbiology 40(2):213-223.

Porrozzi, R. et al. (May 2007). "Comparative Evaluation of Enzyme-Linked Immunosorbent Assays Based on Crude and Recombinant Leishmanial Antigens for Serodiagnosis of Symptomatic and Asymptomatic Leishmania infantum Visceral Infections in Dogs," Clinical and Vaccine Immunology 14( 5):544-548.

Reed, S.G. et al. (Mar. 1, 1987). "Identification of Specific and Cross-Reactive Antigens of Leishmania donovani chagasi by Human Infection Sera," The Journal of Immunology 138(5):1596-1601.

Reed, S.G. et al. (1990). "An Improved Serodiagnostic Procedure for Visceral Leishmaniasis," Am. J. Trop. Med. Hyg. 43(6):632-639.

Reiner, S.L. (1995). "The Regulation of Immunity to Leishmania Major," Annu. Rev. Immunol. 13:151-177.

Rodrigues, V. Jr. et al. (1992). "Selective Inability of Spleen Antigen Presenting Cells from Leishmania donovani Infected Hamsters to Mediate Specific T Cell Proliferation to Parasite Antigens," Parasite Immunology 14(1):49-58.

Russo. D.M. et al. (Nov. 15, 1991). "Human T Cell Responses to gp63, a Surface Antigen of Leishmania," The Journal of Immunology 147(10):3575-3580.

Seaman, J. et al. (1996). "The Epidemic of Visceral Leishmaniasis in Western Upper Nile, Southern Sudan: Course and Impact from 1984 to 1994," International Journal of Epidemiology 25(4):862-871.

Shapira, M. et al. (1990). "Sequence Analysis and Transcriptional Activation of Heat Shock Protein 83 of Leishmania mexicana amazonensis," Molecular and Biochemical Parasitology 42(2): 247-255.

Sheppard, H.W. et al. (1986). "Cloning of Leishmania donovani Genes Encoding Antigens Recognized During Human Visceral Leishmaniasis," Molecular and Biochemical Parasitology 19:35-43. 11.10 1449.

Singh, S. et al. (Mar. 2005). "Applications of Molecular Methods for Leishmania Control," Expert Review of Molecular Diagnostics 5(2):251-265.

Singh, S. et al. (Dec. 1995). "Diagnostic and Prognostic Value of K39 Recombinant Antigen in Indian Leishmaniasis," Journal of Parasitology 81(6): 1000-1003.

Skeiky, Y.A.W. et al. (Jul. 1992). "Cloning and Expression of Trypanosoma cruzi Ribosomal Protein P0 and Epitope Analysis of Anti-P0 Autoantibodies in Chagas' Disease Patients," Journal of Experimental Medicine 176(1):201-211.

Skeiky, Y.A.W. et al. (Apr. 15, 1993). "Proliferative and Cytokine Responses of Human PBMC to Cloned Leishmania braziliensis Heat Shock and Ribosomal Antigens," Abstract, presented at the Joint Meeting of The American Association of Immunologists and the Clinical Immunology Society, May 21-25, 1993, Denver, CO, The Journal of Immunology 150(8, Part II) Abstract No. 517.

Skeiky, Y.A.W. et al. (May 1994). "Antigens Shared by Leishmania Species and Trypanosoma cruzi: Immunological Comparison of the Acidic Ribosomal P0 Proteins," Infection and Immunity 62(5):1643-1651.

Skeiky, Y.A.W. et al. (Apr. 1995). "A Recombinant Leishmania Antigen that Stimulates Human Peripheral Blood Mononuclear Cells to Express a Th1-Type Cytokine Profile and to Produce Interleukin 12," Journal of Experimental Medicine 181(4):1527-1537.

Soto, M. et al. (Oct. 15, 1993). "Genomic Organization and Expression of Two Independent Gene Arrays Coding for Two Antigenic Acidic Ribosomal Proteins of Leishmania," Journal of Biological Chemistry 268(29):21835-21843.

Soto, M. et al. (1993). "Isolation, Characterization and Analysis of the Expression of the Leishmania ribosomal PO Protein Genes," Molecular and Biochemical Parasitology 61:265-274.

Sundar, S. et al. (Sep. 2002). "Laboratory Diagnosis of Visceral Leishmaniasis," Clinical and Diagnostic Laboratory Immunology 9(5):951-958.

Ulrich, J.T. (1995). "Monophosphoryl Lipid A as an Adjuvant. Past Experiences and New Directions," Pharm. Biotechnol. 6:495-524.

UniProt Accession No. Q25278, last updated Apr. 3, 2013, located at http://www.ncbi.nlm.nih.gov/protein/Q25278, last visited on Aug. 30, 2013, two pages.

U.S. Appl. No. 14/780,494, filed Mar. 28, 2014, by Guderian et al.

U.S. Appl. No. 14/780,504, filed, Mar. 28, 2014, by Duthie et al.

Vinhas, V. et al. (1994). "Characterization of T Cell Responses to Purified Leishmania Antigens in Subjects Infected with Leishmania chagasi," Brazilian J. Med. Biol. Res. 27:1199-1205.

Wallace, G.R. et al. (Jul. 1992). "Mapping of a Visceral Leishmaniasis-Specific Immunodominant B-Cell Epitope of Leishmania donovani Hsp70," Infection and Immunity 60(7):2688-2692.

Webb, J.R. et al. (1996). "Molecular Cloning of a Novel Protein Antigen of Leishmania major that Elicits a Potent Immune Response in Experimental Murine Leishmaniasis," The Journal of Immunology 157:5034-5041.

Webb, J.R. et al. (Jul. 1998). "Human and Murine Immune Responses to a Novel Leishmania major Recombinant Protein Encoded by Members of a Multicopy Gene Family," Infection and Immunity 66(7):3279-3289.

White, A.C. Jr. et al. (1992). "Leishmania chagasi Antigens Recognized in Cured Visceral Leishmaniasis and Asymptomatic Infection," Am. J. Trop. Med. Hyg. 46(2):123-131.

Yang, D.M. et al. (1991). "Identification and Characterization of Host-Protective T-cell Epitopes of a Major Surface Glycoprotein (gp63) from Leishmania major," Immunology 72(1):3-9.

Zhang, Y. et al. (Nov. 1992). "Use of a Recombinant 170-Kilodalton Surface Antigen of Entamoeba histolytica for Serodiagnosis of Amebiasis and Identification of Immunodominant Domains of the Native Molecule," Journal of Clinical Microbiology 30(11):2788-2792.

Zhou, X. et al. (1992). "In Vivo Primary Induction of Virus-Specific CTL by Immunization with 9-mer Synthetic Peptides," Journal of Immunological Methods 153:193-200.

VENEZUELAN HUMAN VL PATIENT SERUM SAMPLE-ELISA COMPARISON OF K28, K39 and K9.

ELISA COMPARISON OF K9, K26, K28 and K39 USING CANINE VL SERUM SAMPLES FROM VENEZUELA.

FUSION PROTEINS AND THEIR USE IN THE DIAGNOSIS AND TREATMENT OF LEISHMANIASIS

CROSS-REFERENCE TO RELATED APPLICATIONS

This application is a continuation application of U.S. patent application Ser. No. 13/560,565, filed Jul. 27, 2012 now U.S. Pat. No. 8,771,710 issued Jul. 8, 2015, which is a continuation application of U.S. patent application Ser. No. 12/497,178, filed Jul. 2, 2009, now U.S. Pat. No. 8,231,881, which claims the benefit under 35 U.S.C. §119(e) of U.S. Provisional Patent Application No. 61/078,255, filed Jul. 3, 2008, the contents of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 712192001802_Sequence_Listing.txt, date recorded: May 22, 2014, size: 57,239 bytes).

BACKGROUND

1. Technical Field

The present invention relates generally to fusion proteins made from a synthetic chimeric gene construct comprising sequences from K26, K39, and K9 and their use in the diagnosis and treatment of leishmaniasis.

2. Description of the Related Art

*Leishmania* organisms are intracellular protozoan parasites of macrophages that cause a wide range of clinical diseases in humans and domestic animals, primarily dogs. In some infections, the parasite may lie dormant for many years. In other cases, the host may develop one of a variety of forms of leishmaniasis. For example, the disease may be asymptomatic or may be manifested as sub-clinical visceral leishmaniasis, which is characterized by mild symptoms of malaise, diarrhea and intermittent hepatomegaly. Patients with sub-clinical or asymptomatic disease usually have low antibody titers, making the disease difficult to detect with standard techniques. Alternatively, leishmaniasis may be manifested as a cutaneous disease, which is a severe medical problem but is generally self-limiting, or as a highly destructive mucosal disease, which is not self-limiting. Finally, and most seriously, the disease may be manifested as an acute visceral infection involving the spleen, liver and lymph nodes, which, if left untreated, is generally a fatal disease. Symptoms of acute visceral leishmaniasis include hepatosplenomegaly, fever, leukopenia, anemia and hypergamma-globulinemia.

Three main clinical variants of this disease are known: cutaneous, mucocutaneous, and visceral. Cutaneous leishmaniasis can manifest itself as a single skin ulceration at the site of the sandfly bite appearing soon after infection or months later as disseminated lesions. Mucocutaneous syndrome develops as the cutaneous form, but progresses months or years later to lesions of the mouth, nose, or pharynx. The major long-term effects of cutaneous and mucocutaneous disease are scarring. Visceral leishmaniasis has an incubation period of 3-6 months and involves the reticuloendothelial system.

Clinical manifestations of visceral leishmaniasis include enlargement of the liver and spleen, fever, anemia, and weight loss. In the absence of treatment, symptomatic visceral disease often ends in death. In recent years, the coexistence of HIV and *Leishmania* species causing visceral disease has resulted in several hundreds of cases of dually infected individuals (Berman, J. D., (1997) Clin. Infect. Dis. 24:684). The World Health Organization recently estimated in 2000 that leishmaniasis affects people in 88 countries, with 350 million at risk of contracting the disease and about two million new cases each year. The devastating impact of this disease is exemplified by the recent epidemic of visceral leishmaniasis in the Sudan, which claimed an estimated 100,000 lives (Seaman, J., et al. (1996) Int. J. Epidemiol. 25:862). This disease is frequently a threat in military operations, as demonstrated by the outbreak of viscerotropic leishmaniasis during the Gulf War (Magill, J., et al. (1993) N Engl J Med 328:1383).

Leishmaniasis is a serious problem in much of the world, including Brazil, China, East Africa, India and areas of the Middle East. The disease is also endemic in the Mediterranean region, including southern France, Italy, Greece, Spain, Portugal and North Africa. The number of cases of leishmaniasis has increased dramatically in the last 20 years, and millions of cases of this disease now exist worldwide. About 2 million new cases are diagnosed each year, 25% of which are visceral leishmaniasis. There are, however, no vaccines or effective treatments currently available.

Leishmaniasis is caused by several species of *Leishmania*. These unicellular organisms of the order Kinetoplastida are related to trypanosomes, the causative organisms of Sleeping Sickness in Africa and Chagas' disease in South America. *Leishmania* parasites commonly exist in two distinct forms, the motile promastigote of the insect vector and the sessile amastigote present in the mammalian host. Promastigotes are transmitted to humans by the bite of infected phlebotomine sandflies, which are found throughout the world's inter-tropical and temperate regions. Upon delivery into the mammalian host, promastigotes infect macrophages of the reticuloendothelial system and transform into amastigotes.

Accurate diagnosis of leishmaniasis is frequently difficult to achieve. There are 20 species of *Leishmania* that infect humans, including *L. donovani, L. chagasi, L. infantum, L. major, L. amazonensis, L. braziliensis, L. panamensis, L. mexicana, L. tropica*, and *L. guyanensis*, and there are no distinctive signs or symptoms that unambiguously indicate the presence of *Leishmania* infection. Parasite detection methods have been used, but such methods are neither sensitive nor clinically practical. Current skin tests typically use whole or lysed parasites. Such tests are generally insensitive, irreproducible and prone to cross-reaction with a variety of other diseases. In addition, the preparations employed in such tests are often unstable.

Thus, there is a need for improved methods for the detection of *Leishmania* infection. For example, there is a need in the art for more sensitive and specific methods for detecting *Leishmania* infection, and for identifying those asymptomatic *Leishmania* infections that are likely to progress to acute visceral infections. The present invention fulfills these needs and further provides other related advantages.

BRIEF SUMMARY

The present invention relates generally to compositions comprising at least two heterologous *Leishmania* antigens, fusion polypeptides comprising the antigens, and polynucleotides encoding the antigens and fusions, wherein the *Leishmania* antigens are selected from K39, K26, and/or K9. The present invention also relates methods of using the polypeptides and polynucleotides of the invention in the diagnosis, treatment, and prevention of leishmaniasis. The antigens of the invention, when employed in combination and/or as fusion polypeptides or polynucleotides as described herein, offer improved and unexpected advantages, and are particularly useful in the context of leishmaniasis diagnostics and vaccine development.

Therefore, according to one embodiment, the present invention provides an isolated fusion polypeptide comprising two or more *Leishmania* antigens selected from the group consisting of K26, K39, and K9, or immunogenic portions or variants thereof. In a related embodiment, an isolated fusion polypeptide comprises at least all three of the above *Leishmania* antigens, wherein at least one of the antigens is isolated from *Leishmania donovani*.

In particular embodiments, fusion polypeptides of the invention comprise a first immunogenic portion comprising at least residues 142-267 of K26 (SEQ ID NO: 5); a second immunogenic portion comprising at least residues 2110-2343 of K39 (SEQ ID NO: 6); and a third immunogenic portion comprising at least residues 1-399 of K9 (SEQ ID NO: 7). In more particular embodiments, a fusion polypeptide of the present invention comprises an amino acid sequence as set forth in amino acid residues 10-262 of SEQ ID NO: 8. In certain embodiments, the fusion polypeptide comprises an N-terminal amino acid sequence of MHHHHHHTS (SEQ ID NO: 21). In certain other embodiments, the fusion polypeptide comprises an amino acid sequence as set forth in SEQ ID NO: 8.

In various embodiments, the present invention provides isolated polynucleotides encoding a fusion polypeptide of the present invention.

The present invention also provides an isolated antibody, or antigen binding fragment that specifically bind a fusion polypeptide as described herein throughout.

In another embodiment, the invention contemplates, pharmaceutical composition comprising a fusion polypeptide of the present invention, or an isolated antibody or antigen binding fragment recognizing a fusion polypeptide of the present invention, or a polynucleotide encoding a fusion polypeptide of the present invention, in combination with a physiologically acceptable carrier.

In a related embodiment, the present invention contemplates vaccine compositions comprising a fusion polypeptide of the present invention, or an isolated antibody or antigen binding fragment recognizing a fusion polypeptide of the present invention, or a polynucleotide encoding a fusion polypeptide of the present invention, in combination with a non-specific immune response enhancer.

In particular embodiments, the present invention provides methods to detect asymptomatic or sub-clinical *Leishmania* infection in a biological sample selected from the group consisting of sera, blood, and saliva, comprising: contacting a biological sample with a fusion polypeptide comprising two or more *Leishmania* antigens selected from the group consisting of K26, K39, and K9, or immunogenic portions thereof; and detecting in the biological sample the presence of antibodies that bind to the fusion polypeptide, thereby detecting asymptomatic sub-clinical or active *Leishmania* infection in the biological sample. In more particular embodiments, a method to detect asymptomatic or sub-clinical *Leishmania* infection in a biological sample employs a fusion polypeptide comprising: a first immunogenic portion comprising at least residues 142-267 of K26 (SEQ ID NO: 5); a second immunogenic portion comprising at least residues 2110-2343 of K39 (SEQ ID NO: 6); and a third immunogenic portion comprising at least residues 1-399 of K9 (SEQ ID NO: 7). In yet more particular embodiments, the fusion polypeptide comprises an amino acid sequence as set forth in residues 10-262 of SEQ ID NO: 8. In yet more particular related embodiments, the fusion polypeptide further comprises an N-terminal amino acid sequence of MHHHHHHTS (SEQ ID NO: 21).

In related embodiments, methods for detecting asymptomatic or sub-clinical *Leishmania* infection in a biological sample use a fusion polypeptide bound to a solid support, wherein the solid support may comprise, for example, nitrocellulose, latex or a plastic material. In certain embodiments, the methods further comprise i) removing unbound sample from a solid support; ii) adding a detection reagent to the solid support; and iii) determining the level of detection reagent bound to the solid support, relative to a predetermined cutoff value, thereby detecting asymptomatic or sub-clinical *Leishmania* infection in the biological sample.

In various embodiments, the present invention provides methods of identifying a patient afflicted with asymptomatic or sub-clinical visceral leishmaniasis that is likely to develop acute visceral leishmaniasis, comprising: contacting a biological sample obtained from a patient afflicted with asymptomatic or sub-clinical visceral leishmaniasis with a first polypeptide that is a fusion polypeptide comprising two or more *Leishmania* antigens selected from the group consisting of K26, K39, and K9, or immunogenic portions thereof, the biological sample being selected from the group consisting of sera, blood, and saliva; and independently contacting the biological sample with a second polypeptide comprising an amino acid sequence as set forth in SEQ ID NOs: 6, 10 or 11; and detecting in the sample the presence of antibodies that bind to at least one of the first and second polypeptides, thereby identifying a patient afflicted with asymptomatic or sub-clinical visceral leishmaniasis that is likely to develop acute visceral leishmaniasis.

In particular embodiments, the methods of identifying a patient afflicted with asymptomatic or sub-clinical visceral leishmaniasis that is likely to develop acute visceral leishmaniasis employ a fusion polypeptide comprising a first immunogenic portion comprising at least residues 142-267 of K26 (SEQ ID NO: 5); a second immunogenic portion comprising at least residues 2110-2343 of K39 (SEQ ID NO: 6); and a third immunogenic portion comprising at least residues 1-399 of K9 (SEQ ID NO: 7). In yet more particular embodiments, the fusion polypeptide comprises an amino acid sequence as set forth in amino acid residues 10-262 of SEQ ID NO: 8. In yet more particular related embodiments, the fusion polypeptide further comprises an N-terminal amino acid sequence of MHHHHHHTS (SEQ ID NO: 21).

In related embodiments, methods of identifying a patient afflicted with asymptomatic or sub-clinical visceral leishmaniasis that is likely to develop acute visceral leishmaniasis employ a fusion polypeptide bound to a solid support, wherein the solid support may comprise, for example, nitrocellulose, latex or a plastic material. In certain related embodiments, the methods further comprise i) removing unbound sample from each solid support; ii) adding a detection reagent to each solid support; and iii) comparing the level of detection reagent bound to each solid support, relative to a predetermined cutoff value, therefrom identifying a patient afflicted with asymptomatic or sub-clinical leishmaniasis that is likely to develop acute visceral leishmaniasis.

In particular embodiments, the detection reagent comprises a reporter group conjugated to a binding agent. In related embodiments the binding agent is selected from the group consisting of anti-immunoglobulin, Protein G, Protein A and lectins. In further related embodiments, the reporter group is selected from the group consisting of radioisotopes, fluorescent groups, luminescent groups, enzymes, colloidal gold, biotin and dye particles.

In various other embodiments, the present invention provides diagnostic kits for detecting asymptomatic or sub-clinical visceral leishmaniasis in a biological sample. In particular embodiments, kits for detecting asymptomatic or sub-clinical visceral leishmaniasis in a biological sample, wherein the sample is selected from the group consisting of sera, blood, and saliva, comprise a fusion polypeptide comprising two or more *Leishmania* antigens selected from the group consisting of K26, K39, and K9, or immunogenic portions thereof; and a detection reagent.

In certain embodiments, a diagnostic kit for identifying a patient afflicted with asymptomatic or sub-clinical visceral leishmaniasis that is likely to develop acute visceral leishmaniasis, contains a first polypeptide that is a fusion polypeptide comprising two or more *Leishmania* antigens selected from the group consisting of K26, K39, and K9, or immunogenic portions thereof; and a second polypeptide comprising an amino acid sequence as set forth in SEQ ID NOs: 10 or 11; and a detection reagent.

Kits of the present invention may further comprise, a detection reagent comprising a reporter group conjugated to a binding agent and/or a binding agent is selected from the group consisting of anti-immunoglobulin, Protein G, Protein A and lectins and/or a reporter group is selected from the group consisting of radioisotopes, fluorescent groups, luminescent groups, enzymes, colloidal gold, biotin and dye particles.

BRIEF DESCRIPTION OF THE SEQUENCE IDENTIFIERS

Figure 1:
FIG. 1 shows a schematic diagram of the K28 fusion gene construct, which comprises an N-terminal 9 amino acid motif comprising a 6×HIS tag (i.e., 6 histidine residues), polynucleotides 142-267 of an LdK26 gene sequence (SEQ ID NO: 1), polynucleotides 2110-2343 of an LdK39 gene sequence (SEQ ID NO: 2), and polynucleotides 1-399 of an LdK9 gene sequence (SEQ ID NO: 3).

SEQ ID NO: 1 represents polynucleotides 142-267 of a *L. donovani* K26 gene sequence, which encode an immunogenic portion of the K26 antigen.

SEQ ID NO: 2 represents polynucleotides 2110-2343 of a *L. donovani* K39 gene sequence, which encode an immunogenic portion of the K39 antigen.

SEQ ID NO: 3 represents polynucleotides 1-399 of a *L. donovani* K9 gene sequence, which encodes an immunogenic portion and the full-length K9 antigen.

SEQ ID NO: 4 represents the polynucleotide sequence of a synthetic gene, K28, which comprises an N-terminal 9 amino acid motif comprising a 6×HIS tag, the polynucleotide sequence of SEQ ID NO: 1, fused to the polynucleotide sequence of SEQ ID NO:2, which is fused to the polynucleotide sequence of SEQ ID NO3. The ORF begins at nucleotide 4.

SEQ ID NO: 5 represents the amino acid sequence of an immunogenic polypeptide encoded by polynucleotides 142-267 of a *L. donovani* K26 antigen.

SEQ ID NO: 6 represents the amino acid sequence of an immunogenic polypeptide encoded by polynucleotides 2110-2343 of a *L. donovani* K39 antigen.

SEQ ID NO: 7 represents the amino acid sequence of the immunogenic full-length polypeptide encoded by polynucleotides 1-399 of a *L. donovani* K9 antigen.

SEQ ID NO: 8 represents the amino acid sequence of the K28 polypeptide encoded by SEQ ID NO: 4.

SEQ ID NO: 9 represents the amino acid sequence of a single repeat unit of a *L. donovani* K26 antigen.

SEQ ID NO: 10 represents the amino acid sequence of a single repeat unit of a *L. donovani* K39 antigen.

SEQ ID NO: 11 represents the amino acid sequence of a single repeat unit of a *L. donovani* K39 antigen.

SEQ ID NO: 12 represents a polynucleotide sequence encoding a single repeat unit of a *L. donovani* K26 antigen according to SEQ ID NO: 9.

SEQ ID NO: 13 represents a polynucleotide sequence encoding a single repeat unit of a *L. donovani* K26 antigen according to SEQ ID NO: 9.

SEQ ID NO: 14 represents a polynucleotide sequence encoding the single repeat unit of a *L. donovani* K39 antigen according to SEQ ID NO: 10.

SEQ ID NO: 15 represents a polynucleotide sequence encoding the single repeat unit of a *L. donovani* K39 antigen according to SEQ ID NO: 11.

SEQ ID NO: 16 represents the full-length polynucleotide sequence of a *L. donovani* K26 gene.

SEQ ID NO: 17 represents the full-length polynucleotide sequence of a *L. donovani* K39 gene.

SEQ ID NO: 18 represents the full-length polynucleotide sequence of a *L. donovani* K9 gene.

SEQ ID NO: 19 represents the amino acid sequence encoded by SEQ ID NO: 16.

SEQ ID NO: 20 represents the amino acid sequence encoded by SEQ ID NO: 17.

SEQ ID NO: 21 represents an illustrative N-terminal histidine tag used in the recombinant production of polypeptides of the present invention.

DETAILED DESCRIPTION

*Leishmania* Antigens and Fusions Thereof

The present invention relates generally to compositions and methods of using *Leishmania* antigens. The compositions of the present invention generally comprise at least two heterologous antigens or immunogenic portion thereof of a *Leishmania* species. *Leishmania* antigen sequences can be obtained, for example, from the National Center for Biotechnology Information (NCBI) database for a variety of *Leishmania* species, including *L. donovani, L. chagasi, L. infantum, L. major, L. amazonensis, L. venezuelensis, L. braziliensis, L. panamensis, L. mexicana, L. tropica*, and *L. guyanensis*.

In one aspect, the present invention provides isolated *Leishmania* polypeptides, as described herein, including fusion polypeptides, and compositions containing the same. Generally, a polypeptide of the present invention will be an isolated polypeptide and may comprise a polypeptide fragment (e.g., an antigenic/immunogenic portion), multiple polypeptide fragments (e.g., a fusion polypeptide), or a full-length polypeptide of an amino acid sequence from two or more of the *Leishmania* genes, including, but not limited to K26, K39, and/or K9. One of ordinary skill in the art would appreciate that antigenic polypeptide fragments could also be obtained from those already available in the art. Polypeptides of the invention, antigenic/immunogenic fragments thereof, and other variants may be prepared using conventional recombinant and/or synthetic techniques.

In certain embodiments, the polypeptides of the present invention are fusion polypeptides. In particular embodiments, the fusion polypeptides comprise K26, K39, and/or K9 antigens or immunogenic portions thereof, which are antigenic/immunogenic, i.e., they react detectably within an immunoassay (such as an ELISA or T cell stimulation assay) with antisera and/or T cells from an infected subject. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory Press, 1988. In one illustrative example, a polypeptide of the present invention (e.g., a fusion polypeptide) may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, the fusion polypeptides of the present invention may comprise antigenic or immunogenic portions or fragments of the *Leishmania* K26, K39, and/or K9 polypeptides disclosed herein. An "immunogenic portion," as used herein, is a fragment of an immunogenic polypeptide of the invention that itself is immunologically reactive (i.e., specifically binds) with the B-cells and/or T cell surface antigen receptors that recognize the polypeptide. Immunogenic portions may generally be identified using well known techniques, such as those summarized in Paul, *Fundamental Immunology*, 5th ed., Lippincott Williams & Wilkins, 2003 and references cited therein. Such techniques include screening polypeptides for the ability to react with antigen-specific antibodies, antisera and/or T cell lines or clones. As used herein, antisera and antibodies are "antigen-specific" if they specifically bind to an antigen (i.e., they react with the protein in an immunoassay, and do not react detectably with unrelated proteins). Such antisera and antibodies may be prepared as described herein and using well-known techniques.

In a particular embodiment, an antigenic/immunogenic portion or polypeptide fragment of a fusion polypeptide of the present invention is a portion that reacts with antisera and/or T cells at a level that is not substantially less than the reactivity of the full-length fusion polypeptide (e.g., in an ELISA and/or T cell reactivity assay). Preferably, the level of immunogenic activity of the antigenic/immunogenic portion within a fusion polypeptide is at least about 50%, preferably at least about 70% and most preferably greater than about 90% of the immunogenicity for the full-length fusion polypeptide. In some instances, preferred immunogenic portions will be identified that have a level of immunogenic activity greater than that of the corresponding full-length fusion polypeptide, e.g., having greater than about 100% or 150% or more immunogenic activity. In particular embodiments, the immunogenicity of the full-length fusion polypeptide will have additive immunogenicity contributed by of each of the antigenic/immunogenic portions contained therein.

A fusion polypeptide of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof. In particular embodiments, the polypeptide is a fusion polypeptide as described herein.

In another embodiment of the invention, fusion polypeptides are provided that comprise two or more polypeptides that are capable of eliciting T cells and/or antibodies that are immunologically reactive with two or more polypeptides described herein, or two or more polypeptides encoded by contiguous polynucleotide sequences contained in the polynucleotide sequences disclosed herein, or immunogenic fragments or variants thereof, or to two or more polynucleotide sequences which hybridize to two or more of these sequences under conditions of moderate to high stringency.

The present invention also provides fusion polypeptides comprising fragments, of K26, K29, and/or K9 polypeptides, including antigenic/immunogenic fragments comprising at least about 5, 10, 15, 20, 25, 50, 75, 100, 150, 200, 250, 300, or 350 contiguous amino acids, or more, including all intermediate lengths, of a *Leishmania* K26, K39, and/or K9 antigen, such as those set forth herein, or those encoded by a polynucleotide sequence set forth herein.

In another aspect, fusion polypeptides of the present invention contain multiple copies of polypeptide fragments, repeats of polypeptide fragments, or multimeric polypeptide fragments, including antigenic/immunogenic fragments such as *Leishmania* K26, K39, and/or K9 polypeptides, comprising at least about 1, 2, 3, 4, 5, 6, 7, 8, 9, 10 or more contiguous fragments, in any order, and including all lengths of a polypeptide composition set forth herein, or those encoded by a polynucleotide sequence set forth herein. In another aspect, fusion polypeptides of the present invention may comprise two or more *Leishmania* antigen fragments as recited in SEQ ID NOs: 5-7, and 9-11. In a related aspect, the fusion polypeptide comprises the amino acid sequence set forth in SEQ ID NO: 8 or amino acids 10-262 of SEQ ID NO: 8.

In yet another aspect, the present invention provides fusion polypeptides comprising two or more variants of the *Leishmania* K26, K29, and/or K9 polypeptides described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequence set forth herein. Preferably, such variants will have the same, similar or improved immunological activity relative to a native K26, K29, and/or K9 sequence.

A polypeptide "variant," as the term is used herein, is a polypeptide that typically differs from a polypeptide specifically disclosed herein (e.g., *Leishmania* K26, K29, and/or K9 polypeptides) in one or more substitutions, deletions, additions and/or insertions. Such variants may be naturally occurring or may be synthetically generated, for example, by modifying one or more of the above polypeptide sequences of the invention and evaluating their immunogenic activity as described herein using any of a number of techniques well known in the art.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4:2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-Histidine tag (6×His), GST, MBP, TAP/TAG, FLAG epitope, MYC epitope, V5 epitope, VSV-G epitope, etc.), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) CAB/OS 5:151-153; Myers, E. W. and Muller W. (1988) *CABIOS* 4:11-17; Robinson, E. D. (1971) Comb. Theor 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Nat'l Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Nat'l Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

In certain preferred embodiments of the invention, there are provided *Leishmania* fusion polypeptides, and polynucleotides encoding fusion polypeptides, wherein the fusion polypeptides comprise two or more of K26, K39, and/or K9 polypeptide sequences or immunogenic portions thereof. Fusion polypeptide and fusion proteins refer to a polypeptide having at least two heterologous *Leishmania* sp. polypeptides, such as *Leishmania donovani* polypeptides, covalently linked, either directly or via an amino acid linker. The K26, K39, and/or K9 antigenic sequences may, but need not, be derived from the same *Leishmania* species. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order and may contain multiple copies of, repeats of, or multimers of each or any of the polypeptides comprising the fusion protein. Fusion polypeptides or fusion proteins can also include conservatively modified variants, polymorphic variants, alleles, mutants, subsequences, interspecies homologs, and immunogenic fragments of the antigens that make up the fusion protein. In particular embodiments, fusion polypeptides of the present invention may comprise one or more *Leishmania* antigen fragments as recited in SEQ ID NOs: 5-7, and 9-11. In a related embodiment, the fusion polypeptide comprises the amino acid sequence set forth in SEQ ID NO: 8 or amino acids 10-262 of SEQ ID NO: 8.

Antigens from other *Leishmania* species that correspond to *Leishmania donovani* antigens may also be used and can be identified, e.g., using sequence comparison algorithms, as described herein, or other methods known to those of skill in the art, e.g., hybridization assays and antibody binding assays.

The fusion polypeptides of the invention generally comprise at least two antigenic/immunogenic portions or fragments from K26, K39, and/or K9 polypeptides as described herein, and may further comprise other unrelated sequences, such as a sequence that assists in providing T helper epitopes (an immunological fusion partner), preferably T helper epitopes recognized by humans, or that assists in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners may include affinity tags such as V5, 6×HIS, MYC, FLAG, and GST, which facilitate purification of the protein. It would be understood by one having ordinary skill in the art that those unrelated sequences may, but need not, be present in a fusion polypeptide used in accordance with the present invention.

Fusion proteins may generally be prepared using standard techniques. Preferably, a fusion protein is expressed as a recombinant protein. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39 46 (1985); Murphy et al., Proc. Natl. Acad. Sci. USA 83:8258 8262 (1986); U.S. Pat. No. 4,935,233 and U.S. Pat. No. 4,751, 180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Within preferred embodiments, an immunological fusion partner for use in a fusion polypeptide of the invention is derived from protein D, a surface protein of the gram-negative bacterium *Haemophilus* influenza B (WO 91/18926). Preferably, a protein D derivative comprises approximately the first third of the protein (e.g., the first N-terminal 100 110 amino acids), and a protein D derivative may be lipidated. Within certain preferred embodiments, the first 109 residues of a lipoprotein D fusion partner is included on the N-terminus to provide the fusion polypeptide with additional exogenous T cell epitopes and to increase the expression level in *E. coli* (thus functioning as an expression enhancer). The lipid tail ensures optimal presentation of the antigen to antigen presenting cells. Other fusion partners include the non-structural protein from *influenzae* virus, NS1 (hemaglutinin). Typically, the N-terminal 81 amino acids are used, although different fragments that include T-helper epitopes may be used. In another embodiment, an immunological fusion partner comprises an amino acid sequence derived from the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798 (1992)). Within a preferred embodiment, a repeat portion of LYTA may be incorporated into fusion polypeptides of the present invention, as described herein. A repeat portion is found in the C-terminal region starting at residue 178. A particularly preferred repeat portion incorporates residues 188-305.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

In certain embodiments, the fusion polypeptides of the invention will comprise at least one epitope from each of K26, K39 and K9. Epitopes may generally be determined by generating polypeptides containing portions or fragments of the sequence and evaluating the reactivity of the polypeptides with sera from *Leishmania*-infected individuals using, for example, an enzyme linked immunosorbent assay (ELISA). Suitable assays for evaluating reactivity of a polypeptide with *Leishmania*-infected sera are described in more detail below. Within such representative assays, portions of the sequence that generate a signal that differentiates between positive and negative sera in a manner substantially similar to that of the full length are considered to contain an epitope. In other words, a portion of the antigen that contains an epitope will generate a signal indicating *Leishmania* infection in substantially all (i.e., at least about 80%, and preferably at least about 90%) of the biological samples for which such infection would be indicated using the full length antigen and will generate a signal indicating the absence of *Leishmania* infection in substantially all of those samples that would be negative with the full length polypeptide.

In a related aspect, fusion polypeptides comprising epitopes of multiple *Leishmania* polypeptides are disclosed. In certain particular embodiments, epitopes of different *Leishmania* polypeptides, repeats, or variants thereof, are joined though a peptide linkage into a single amino acid chain. The epitopes may be joined directly (i.e., with no intervening amino acids) or may be joined by way of a linker sequence (e.g., Gly-Cys-Gly) that does not significantly alter the antigenic properties of the epitopes. In particular embodiments the fusion polypeptide is derived from two or more antigenic/immunogenic portions or fragments. In another aspect, fusion polypeptides of the present invention may comprise two or more *Leishmania* antigen fragments as recited in SEQ ID NOs: 5-7 and 9-11. In a related aspect, the fusion polypeptide comprises the amino acid sequence set forth in SEQ ID NO: 8 or amino acid residues 10-262 of SEQ ID NO: 8.

The fusion polypeptides of this invention may be generated using techniques well known to those of ordinary skill in the art. Polypeptides of the present invention having fewer than about 100 amino acids, and generally fewer than about 50 amino acids, can be synthesized using, for example, the Merrifield solid-phase synthesis method, where amino acids are sequentially added to a growing amino acid chain (Merrifield, *J. Am. Chem. Soc.* 85:2149-2146, 1963). Equipment for automated synthesis of polypeptides is commercially available from suppliers such as Applied Biosystems, Inc., Foster City, Calif. Thus, for example, *Leishmania* K26, K39 and K9 antigens, or portions thereof, may be synthesized by this method.

Alternatively, the polypeptides of this invention may be prepared by expression of recombinant DNA encoding the polypeptide in cultured host cells. Preferably, the host cells are *E. coli*, yeast, an insect cell line (such as *Spodoptera* or *Trichoplusia*) or a mammalian cell line, including (but not limited to) CHO, COS, HEK-293T and NS-1. The DNA sequences expressed in this manner may encode naturally occurring proteins, and fusion proteins comprising *Leishmania* antigens such as K26, K9 and/or K39, portions thereof, and repeats or other variants of such proteins. Expressed fusion polypeptides of this invention are generally isolated in substantially pure form. Preferably, the fusion polypeptides are isolated to a purity of at least 80% by weight, more preferably, to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography.

Polynucleotide Compositions

The present invention also provides isolated polynucleotides, particularly those encoding the fusion polypeptides of the invention, as well as compositions comprising such polynucleotides. As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, fusion polypeptides, peptides and the like. Such segments may be naturally isolated, recombinant, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a *Leishmania* antigen or a portion thereof) or may comprise a variant, or a biological or antigenic functional equivalent of such a sequence. In particular embodiments polynucleotides may encode for two or more antigenic/immunogenic portions, fragments, or variants derived from the *Leishmania* K26, K39, and/or K9 antigens. In certain embodiment, polynucleotides encoding fusion polypeptides of the present invention may encode two or more *Leishmania* antigen fragments as recited in SEQ ID NOs: 5-7, and 9-11. In a related aspect, the fusion polypeptide is encoded by polynucleotides encoding the amino acid sequence set forth in SEQ ID NO: 8 or amino acids 10-262 of SEQ ID NO: 8.

Polynucleotide variants may contain one or more substitutions, additions, deletions and/or insertions, as further described below, preferably such that the immunogenicity of the encoded polypeptide is not diminished, relative to the native protein. The effect on the immunogenicity of the encoded polypeptide may generally be assessed as described herein. The term "variants" also encompasses homologous genes of xenogenic origin.

In additional embodiments, isolated fusion polynucleotides will comprise various lengths of contiguous stretches of sequence identical to or complementary to two or more K26, K39, and or K9, such as those sequences disclosed herein, portions or variants thereof. For example, polynucleotides are provided by this invention that comprise at least about 15, 20, 30, 40, 50, 75, 100, 150, 200, 300, 400, 500 or 1000 or more contiguous nucleotides of two or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The fusion polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed; with the total length preferably being limited by the ease of preparation and use in the intended recombinant DNA protocol.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

*Leishmania* polynucleotides and fusions thereof may be prepared, manipulated and/or expressed using any of a variety of well established techniques known and available in the art. For example, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide of the present invention.

As will be understood by those of skill in the art, it may be advantageous in some instances to produce fusion polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter fusion polypeptide encoding sequences for a variety of reasons, including but not limited to, alterations which modify the cloning, processing, expression and/or immunogenicity of the gene product.

In order to express a desired fusion polypeptide comprising two or more antigenic/immunogenic fragments or portions of K26, K39, and/or K9 polypeptides, a nucleotide sequence encoding the fusion polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (2001), and Ausubel et al., Current Protocols in Molecular Biology (January 2008, updated edition).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional E. coli cloning and expression vectors such as PBLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, J. Biol. Chem. 264:5503-5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al., Methods Enzymol. 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, EMBO J. 6:307-311 (1987)). Alternatively, plant promoters such as the small subunit of RUBISCO or heat shock promoters may be used (Coruzzi et al., EMBO J. 3:1671-1680 (1984); Broglie et al., Science 224:838-843 (1984); and Winter et al., Results Probl. Cell Differ. 17:85-105 (1991)). These constructs can be introduced into plant cells by direct DNA transformation or pathogen-mediated transfection. Such techniques are described in a number of generally available reviews (see, e.g., Hobbs in McGraw Hill, Yearbook of Science and Technology, pp. 191-196 (1992)).

An insect system may also be used to express a polypeptide of interest. For example, in one such system, Autographa californica nuclear polyhedrosis virus (AcNPV) is used as a vector to express foreign genes in Spodoptera frugiperda cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, S. frugiperda cells or Trichoplusia larvae in which the polypeptide of interest may be expressed (Engelhard et al., Proc. Natl. Acad. Sci. U.S.A. 91:3224-3227 (1994)).

In mammalian host cells, a number of viral-based expression systems are generally available. For example, in cases where an adenovirus is used as an expression vector, sequences encoding a polypeptide of the present invention may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, Proc. Natl. Acad. Sci. U.S.A. 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a fusion polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed fusion protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a fusion polynucleotide of the present invention may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk- or aprt- cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

In addition to recombinant production methods, fusion polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments, for example, two or more antigenic/immunogenic fragments from *Leishmania* K26, K39, and/or K9 antigens, may be chemically synthesized separately and combined using chemical methods to produce the full length molecule.

Diagnostic Methods and Kits

In another aspect, this invention provides compounds and methods for detecting leishmaniasis in individuals and in blood supplies. In a particular embodiment, the individual is a mammal. In a more particular embodiment the mammal is a human or canine.

In one aspect, there are provided methods for detecting asymptomatic or sub-clinical visceral leishmaniasis in a biological sample, comprising: (a) contacting a biological sample with a fusion polypeptide as described herein, e.g., comprising at least two heterologous *Leishmania* antigens, wherein the *Leishmania* antigens are selected from K39, K26, and/or K9 or a variant thereof that differs only in conservative substitutions and/or modifications; and (b) detecting in the biological sample the presence of antibodies that bind to the fusion polypeptide, thereby detecting asymptomatic or sub-clinical visceral *Leishmania* infection in the biological sample.

In a particular aspect, the present invention provides methods for detecting asymptomatic or sub-clinical visceral leishmaniasis in a biological sample, comprising: (a) contacting a biological sample with a fusion polypeptide as described herein, e.g., comprising at least two heterologous *Leishmania* antigens, wherein the *Leishmania* antigens are selected from K39, K26, and/or K9 polypeptide sequences according any of SEQ ID NOs: 5-7, and 9-11, in any combination, or a variant thereof that differs only in conservative substitutions and/or modifications; and (b) detecting in the biological sample the presence of antibodies that bind to the polypeptide, thereby detecting asymptomatic or sub-clinical visceral *Leishmania* infection in the biological sample. In related embodiments, at least one of the *Leishmania* antigens K26, K39, and K9 is from the *Leishmania donovani* species.

In certain aspects, the present invention provides methods for detecting visceral *Leishmania* infection in a biological sample, comprising: (a) contacting a biological sample with a fusion polypeptide as described herein, e.g., comprising at least two heterologous *Leishmania* antigens, wherein the fusion protein comprises the amino acid sequence set forth in SEQ ID NO: 8 or amino acids 10-262 of SEQ ID NO: 8, or variants thereof that differ only in conservative substitutions and/or modifications; and (b) detecting in the biological sample the presence of antibodies that bind to the polypeptide, thereby detecting visceral *Leishmania* infection in the biological sample.

In yet another related aspect, methods are provided for identifying a patient afflicted with asymptomatic or sub-clinical visceral leishmaniasis that is likely to develop acute visceral leishmaniasis. In one embodiment, the method comprises: (a) contacting a biological sample obtained from a patient afflicted with asymptomatic or sub-clinical visceral leishmaniasis with a fusion polypeptide as described herein, e.g., comprising at least two heterologous *Leishmania* antigens, wherein the *Leishmania* antigens are selected from K39, K26, and/or K9 or a variant thereof that differs only in conservative substitutions and/or modifications; (b) detecting in the biological sample obtained from a patient the presence of antibodies that bind to the fusion polypeptide in step (a), thereby identifying a patient afflicted with asymptomatic or sub-clinical visceral leishmaniasis that is likely to develop acute visceral leishmaniasis (VL).

Within related aspects, diagnostic kits for diagnosing leishmaniasis are provided. In one embodiment, for example, there are provided kits for detecting visceral leishmaniasis in a biological sample, comprising: (a) a fusion polypeptide as described herein, e.g., comprising at least two heterologous *Leishmania* antigens, wherein the *Leishmania* antigens are selected from K39, K26, and/or K9 or a variant thereof that differs only in conservative substitutions and/or modifications; and (b) detecting in the biological sample the presence of antibodies that bind to the polypeptide, thereby detecting visceral leishmaniasis in the biological sample.

In yet another related aspect, methods are provided for identifying a patient afflicted with asymptomatic or sub-clinical visceral leishmaniasis that is likely to develop acute visceral leishmaniasis. In one embodiment, the method comprises: (a) contacting a biological sample obtained from a patient afflicted with asymptomatic or sub-clinical leishmaniasis with a fusion polypeptide as described herein, e.g., comprising at least two heterologous *Leishmania* antigens, wherein the *Leishmania* antigens are selected from K39, K26, and/or K9 polypeptide sequences according any of SEQ ID NOs: 5-7 and 9-11, in any combination, or a variant thereof that differs only in conservative substitutions and/or modifications; and (b) detecting in the biological sample obtained from a patient the presence of antibodies that bind to the fusion polypeptide in step (a), thereby identifying a patient afflicted with asymptomatic or sub-clinical visceral leishmaniasis that is likely to develop acute visceral leishmaniasis (VL).

Within related aspects, diagnostic kits for diagnosing leishmaniasis are provided. In one embodiment, there are provided kits for detecting visceral leishmaniasis in a biological sample, comprising: (a) a fusion polypeptide as described herein, e.g., comprising at least two heterologous *Leishmania* antigens, wherein the *Leishmania* antigens are selected from K39, K26, and/or K9 polypeptide sequences according any of SEQ ID NOs: 5-7 and 9-11, in any combination, or a variant thereof that differs only in conservative substitutions and/or modifications; or a variant thereof that differs only in conservative substitutions and/or modifications; and (b) detecting in the biological sample the presence of antibodies that bind to the polypeptide, thereby detecting visceral leishmaniasis in the biological sample.

In yet another related aspect, methods are provided for identifying a patient afflicted with asymptomatic or sub-clinical visceral leishmaniasis that is likely to develop acute visceral leishmaniasis. In one embodiment, the method comprises: (a) contacting a biological sample obtained from a patient afflicted with asymptomatic or sub-clinical leishmaniasis with a fusion polypeptide as described herein, e.g., comprising at least two heterologous *Leishmania* antigens, wherein the fusion protein comprises the amino acid sequence set forth in SEQ ID NO: 8 or amino acids 10-262 of SEQ ID NO: 8, or variants thereof that differ only in conservative substitutions and/or modifications; and (b) detecting in the biological sample the presence of antibodies that bind to the polypeptide, thereby detecting visceral leishmaniasis in the biological sample.

Within related aspects, diagnostic kits for diagnosing leishmaniasis are provided. In one embodiment, there are provided kits for detecting visceral leishmaniasis in a biological sample, comprising: (a) a fusion polypeptide as described herein, e.g., comprising at least two heterologous *Leishmania* antigens, wherein the fusion protein comprises the amino acid sequence set forth in SEQ ID NO: 8 or amino acids 10-262 of SEQ ID NO: 8, or variants thereof that differ only in conservative substitutions and/or modifications; and (b) detecting in the biological sample the presence of antibodies that bind to the polypeptide, thereby detecting visceral leishmaniasis in the biological sample.

In another aspect of this invention, methods are disclosed for detecting and monitoring *Leishmania* infection, as well as for distinguishing among types of *Leishmania* infections, in individuals and blood supplies. In general, *Leishmania* infection may be detected in any biological sample that contains antibodies. Preferably, the sample is blood, serum, plasma, saliva, cerebrospinal fluid, stool, or urine. More preferably, the sample is a blood or serum sample obtained from a patient or a blood supply.

In another aspect, *Leishmania* infection may be detected using a fusion polypeptide comprising two or more polypeptides containing one or more of the epitopes discussed above, repeats, or variants thereof. If multiple epitopes are employed, these epitopes may be present on one or more *Leishmania* antigens. For example, in one aspect, a fusion polypeptide of the present invention comprises two or more K26, K29, and/or K9 antigenic polypeptides. The fusion polypeptide is then used to determine the presence or absence of antibodies to the same antigenic polypeptides in the sample, relative to a predetermined cut-off value.

There are a variety of assay formats known to those of ordinary skill in the art for using a fusion polypeptide to detect antibodies in a sample. See, e.g., Harlow and Lane, Antibodies. A Laboratory Manual, Cold Spring Harbor Laboratory Press, 1988, which is incorporated herein by reference. In a preferred embodiment, the assay involves the use of fusion polypeptide immobilized on a solid support to bind to and remove the antibody from the sample. The bound antibody may then be detected using a detection reagent that binds to the antibody/peptide complex and contains a detectable reporter group. Suitable detection reagents include antibodies that bind to the antibody/polypeptide complex and free polypeptide labeled with a reporter group (e.g., in a semi-competitive assay). Suitable reporter groups include fluorescent labels, enzyme labels, radioisotopes, chemiluminescent labels, electrochemiluminescent labels, bioluminescent labels, polymers, polymer particles, metal particles, haptens, and dyes. Alternatively, a competitive assay may be utilized, in which an antibody that binds to a fusion polypeptide of the present invention labeled with a reporter group and allowed to bind to the immobilized fusion polypeptide after incubation of the fusion polypeptide with the sample. The extent to which components of the sample inhibit the binding of the labeled antibody to the fusion polypeptide is indicative of the reactivity of the sample with the immobilized fusion polypeptide.

The solid support may be any material known to those of ordinary skill in the art to which the fusion polypeptide may be attached. For example, the support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The fusion polypeptide may be bound to the solid support using a variety of techniques known to those in the art, which are amply described in the patent and scientific literature. In the context of the present invention, the term "bound" refers to both non-covalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of fusion polypeptide ranging from about 10 ng to about 1 µg, and preferably about 100 ng, is sufficient to bind an adequate amount of antigen. Nitrocellulose will bind approximately 100 µg of protein per $cm^3$.

Covalent attachment of fusion polypeptide to a solid support may generally be achieved by first reacting the support with a bifunctional reagent that will react with both the support and a functional group, such as a hydroxyl or amino group, on the fusion polypeptide. For example, the fusion polypeptide may be bound to a support having an appropriate polymer coating using benzoquinone or by condensation of an aldehyde group on the support with an amine and an active hydrogen on the polypeptide (see, e.g., Pierce Immunotechnology Catalog and Handbook (1991) at A12-A13).

In certain embodiments, the assay is an enzyme linked immunosorbent assay (ELISA). This assay may be performed by first contacting a fusion polypeptide of the present invention that has been immobilized on a solid support, commonly the well of a microtiter plate, with the sample, such that antibodies to the *Leishmania* antigens of the fusion polypeptide within the sample are allowed to bind to the immobilized fusion polypeptide. Unbound sample is then removed from the immobilized fusion polypeptide and a detection reagent capable of binding to the immobilized antibody-polypeptide complex is added. The amount of detection reagent that remains bound to the solid support is then determined using a method appropriate for the specific detection reagent.

Once the fusion polypeptide is immobilized on the support, the remaining protein binding sites on the support are typically blocked. Any suitable blocking agent known to those of ordinary skill in the art, such as bovine serum albumin (BSA) or Tween 20™ (Sigma. Chemical Co., St. Louis, Mo.) may be employed. The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to permit detection of the presence of antibody within a *Leishmania*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Pectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*Leishmania* antibodies in the sample, the signal detected from the reporter group that remains bound to the solid support is generally compared to a signal that corresponds to a predetermined cut-off value. In one preferred embodiment, the cut-off value is preferably the average mean signal obtained when the immobilized polypeptide is incubated with samples from an uninfected patient. In general, a sample generating a signal that is three standard deviations above the predetermined cut-off value is considered positive (i.e., reactive with the polypeptide). In an alternate preferred embodiment, the cut-off value is determined using a Receiver Operator Curve, according to the method of Sackett et al., Clinical Epidemiology: A Basic Science for Clinical Medicine, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper lefthand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate.

In a related embodiment, the assay is performed in a flow-through or strip test format, wherein the antigen is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized fusion polypeptide. Concentration of detection reagent at the fusion polypeptide indicates the presence of *Leishmania* antibodies in the sample. Typically, the concentration of detection reagent at that site generates a pattern, such as a line, that can be read visually. The absence of such a pattern indicates a negative result. In general, the amount of fusion polypeptide immobilized on the membrane is selected to generate a visually discernible pattern when the biological sample contains a level of antibodies that would be sufficient to generate a positive signal in an ELISA, as discussed above. Preferably, the amount of fusion polypeptide immobilized on the membrane ranges from about 25 ng to about 1 µg, and more preferably from about 50 ng to about 500 ng. Such tests can typically be performed with a very small amount (e.g., one drop) of patient serum or blood.

Of course, numerous other assay protocols exist that are suitable for use with the fusion polypeptides of the present invention. The above descriptions are intended to be exemplary only.

In one aspect of the invention, the assays discussed above may be used to specifically detect visceral leishmaniasis. In this aspect, antibodies in the sample may be detected using a fusion polypeptide comprising the amino acid sequence of two or more antigenic/immunogenic fragments or epitopes of a *Leishmania* K26, K39, and/or K9 antigen. In another aspect, antibodies in the sample may be detected using a fusion polypeptide comprising the amino acid sequence of two or more immunogenic fragments or epitopes as set forth in any of SEQ ID NOs: 5-7 and 9-11. In another aspect, antibodies in, the sample may be detected using a fusion polypeptide comprising the amino acid sequence set forth in SEQ ID NO: 8 or amino acids 10-262 of SEQ ID NO: 8. Preferably, the *Leishmania* antigens are immobilized by adsorption to a solid support such as a well of a microtiter plate or a membrane, as described above, in roughly similar amounts such that the total amount of fusion polypeptide in contact with the support ranges from about 10 ng to about 100 µg. The remainder of the steps in the assay may generally be performed as described above. It will be readily apparent to those of ordinary skill in the art that, by combining polypeptides described herein with other polypeptides that can detect cutaneous and mucosal leishmaniasis, the polypeptides disclosed herein may be used in methods that detect all types of leishmaniasis.

In another aspect of the invention, patients with asymptomatic or sub-clinical VL whose disease is likely to progress to acute visceral leishmaniasis may be distinguished from infected patients whose disease is not likely to progress. Such progression may occur within a year (and typically within 5-12 months) for sub-clinical disease, or within many years in the case of asymptomatic patients. This determination may be made using any of several approaches. In one embodiment, the assay is performed using a polypeptide as described herein, e.g., that comprises at least one repeat unit of the K39 antigen, as set forth in SEQ ID NOs: 6, 10 or 11, for example. In a related embodiment, the polypeptide comprises a K39 repeat unit antigen encoded by the polynucleotide sequence recited in SEQ ID NOs: 2, 14 or 15. While a K39 repeat unit antigen generates a positive result (relative to the predetermined cut-off value) when reacted with sera from more than 97% of patients with acute visceral leishmaniasis, patients with asymptomatic leishmaniasis react very weakly, if at all, with this antigen. Those sera that react weakly are likely to indicate infections that are in the process of progression, or are likely to progress, to acute visceral leishmaniasis (or infections that are in remission or responding to treatment, which may be distinguished based on patient history).

In another embodiment, the assay is separately performed with a fusion polypeptide of the invention, e.g., comprising the amino acid sequence of two or more antigenic/immunogenic fragments or epitopes of a *Leishmania* K26, K39, and/or K9 antigen, such as K28 for example, and with a polypeptide that comprises at least one repeat unit of the K39 antigen. In this embodiment, the optical density (OD) obtained in the assay using the K28 fusion polypeptide is compared to the value obtained using the K39 polypeptide. A significantly higher OD in the assay using the K28 fusion polypeptide, when compared to the OD in the assay using the K39 polypeptide indicates a more robust, reliable detection of an asymptomatic or sub-clinical VL infection. Those asymptomatic or sub-clinical patients for whom both values are relatively high are likely to be in the process of developing acute visceral leishmaniasis (or in the process of recovering from infection). In another aspect, the assay is separately performed with a fusion polypeptide comprising the amino acid sequence of two or more immunogenic fragments or epitopes as set forth in any of SEQ ID NOs: 5-7 and 9-11 and with a polypeptide that comprises at least one repeat unit of a K39 antigen. In another aspect, the assay is separately performed with a fusion polypeptide comprising the amino acid sequence set forth in SEQ ID NO: 8 or amino acids 10-262 of SEQ ID NO: 8, and with a polypeptide that comprises at least one repeat unit of a K39 antigen.

In another embodiment, asymptomatic or sub-clinical patients that are likely to develop acute visceral leishmaniasis may be identified using separate fusion polypeptide (e.g., K28) and K39 polypeptide assays (as described above) that are performed over a period of time. For example, the assays may be performed every 1, 2, 3, 4, 5, or 6 months for a period of months or years. Asymptomatic or sub-clinical patients that are likely to remain asymptomatic or sub-clinical will generally have sera that show a high reactivity with K28 and a low reactivity with the. K39 polypeptide, as discussed above, at each time point. However, patients that are progressing toward acute visceral leishmaniasis will show an increase in the reactivity of both K28 and K39 polypeptides over the time period of the assays. By monitoring an individual patient in this manner, the development of acute visceral leishmaniasis may be identified before other symptoms become apparent. This early identification allows selective treatment of only those asymptomatic patients that are predisposed to develop a more serious form of the disease.

In another aspect of this invention, immobilized fusion polypeptides may be used to purify antibodies that bind thereto. Such antibodies may be prepared by any of a variety of techniques known to those of ordinary skill in the art. See, e.g., Harlow and Land, Antibodies. A Laboratory Manual, Cold Spring Harbor Laboratory Press, 1988. In one such technique, an immunogen comprising a fusion polypeptide of the present invention is initially injected into any of a wide variety of mammals (e.g., mice, rats, rabbits, sheep and goats). In this step, the polypeptide may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic fusion polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In this process, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. One or more polypeptides may be used in the purification process in, for example, an affinity chromatography step.

Monospecific antibodies that bind to a fusion polypeptide comprising two or more immunogenic portions of *Leishmania* K26, K39, and/or K9 antigens may be used, for example, to detect *Leishmania* infection in a biological sample using one of a variety of immunoassays, which may be direct or competitive. Briefly, in one direct assay format, a monospecific antibody may be immobilized on a solid support (as described above) and contacted with the sample to be tested. After removal of the unbound sample, a second monospecific antibody, which has been labeled with a reporter group, may be added and used to detect bound antigen. In an exemplary competitive assay, the sample may be combined with the monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen and the remainder of the sample and antibody is removed. The level of antibody bound to the solid support is inversely related to the level of antigen in the sample. Thus, a lower level of antibody bound to the solid support indicates the presence of *Leishmania* in the sample. Other formats for using monospecific antibodies to detect *Leishmania* in a sample will be apparent to those of ordinary skill in the art, and the above formats are provided solely for exemplary purposes.

Pharmaceutical and Vaccine Compositions

In another aspect, the present invention concerns formulations of one or more of the polynucleotide, fusion polypeptide or other compositions disclosed herein in pharmaceutically-acceptable or physiologically-acceptable solutions for administration to a cell or an animal, either alone, or in combination with one or more other modalities of therapy. Such pharmaceutical compositions are particularly preferred for use as vaccines when formulated with a suitable immuno-stimulant/adjuvant system. The compositions are also suitable for use in a diagnostic context.

It will also be understood that, if desired, the compositions of the invention may be administered in combination with other agents as well, such as, e.g., other proteins or polypeptides or various pharmaceutically-active agents. There is virtually no limit to other components that may also be included, provided that the additional agents do not cause a significant adverse effect upon the objectives according to the invention.

In certain embodiments, the compositions of the invention are used as vaccines and are formulated in combination with one or more immunostimulants. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., Vaccine Design (the subunit and adjuvant approach) (1995).

Any of a variety of immunostimulants may be employed in the vaccines of this invention. For example, an adjuvant may be included. Many adjuvants contain a substance designed to protect the antigen from rapid catabolism, such as aluminum hydroxide or mineral oil, and a stimulator of immune responses, such as lipid A (natural or synthetic), *Bortadella pertussis* or *Mycobacterium* species or *Mycobacterium* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (SmithKline Beecham, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Other illustrative adjuvants useful in the context of the invention include Toll-like receptor agonists, such as TLR7 agonists, TLR7/8 agonists, and the like. Still other illustrative adjuvants include imiquimod, gardiquimod, resiquimod, and related compounds.

Certain vaccines employ adjuvant systems designed to induce an immune response predominantly of the Th1 type. High levels of Th1-type cytokines (e.g., IFN-γ, TNF-α, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within one embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mossman & Coffman, *Ann. Rev. Immunol.* 7:145-173 (1989).

Certain adjuvants for use in eliciting a predominantly Th1-type response include, for example, a combination of monophosphoryl lipid A, preferably 3-de-O-acylated monophosphoryl lipid A (3D-MPL™), together with an aluminum salt (U.S. Pat. Nos. 4,436,727; 4,877,611; 4,866,034; and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352 (1996). Another illustrative adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other illustrative formulations include more than one saponin in the adjuvant combinations of the present invention, for example combinations of at least two of the following group comprising QS21, QS7, Quil A, escin, or digitonin.

In a particular embodiment, the adjuvant system includes the combination of a monophosphoryl lipid A and a saponin derivative, such as the combination of QS21 and 3D-MPL™. adjuvant, as described in WO 94/00153, or a less reactogenic composition where the QS21 is quenched with cholesterol, as described in WO 96/33739. Other formulations comprise an oil-in-water emulsion and tocopherol. Another adjuvant formulation employing QS21, 3D-MPL™ adjuvant and tocopherol in an oil-in-water emulsion is described in WO 95/17210.

Another enhanced adjuvant system involves the combination of a CpG-containing oligonucleotide and a saponin derivative as disclosed in WO 00/09159.

Other illustrative adjuvants include Montanide ISA 720 (Seppic, France), SAF (Chiron, Calif., United States), ISCOMS (CSL), MF-59 (Chiron), the SBAS series of adjuvants (e.g., SBAS-2, AS2', AS2," SBAS-4, or SBAS6, available from SmithKline Beecham, Rixensart, Belgium), Detox, RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Compositions of the invention may also, or alternatively, comprise T cells specific for a *Leishmania* fusion polypeptide as described herein throughout. Such cells may generally be prepared in vitro or ex vivo, using standard procedures. For example, T cells may be isolated from bone marrow, peripheral blood, or a fraction of bone marrow or peripheral blood of a patient. Alternatively, T cells may be derived from related or unrelated humans, non-human mammals, cell lines or cultures.

T cells may be stimulated with a fusion polypeptide comprising, two or more immunogenic portions of *Leishmania* K26, K39, and/or K9 antigens, polynucleotide encoding such a fusion polypeptide, and/or an antigen presenting cell (APC) that expresses such a fusion polypeptide. Such stimulation is performed under conditions and for a time sufficient to permit the generation of T cells that are specific for the fusion polypeptide. Preferably, the fusion polypeptide or polynucleotide is present within a delivery vehicle, such as a microsphere, to facilitate the generation of specific T cells.

T cells are considered to be specific for a fusion polypeptide of the invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070 (1994)). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the invention (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNFα or IFN-γ) is indicative of T cell activation (see Coligan et al., *Current Protocols in Immunology*, vol. 1 (1998)). T cells that have been activated in response to a fusion polypeptide, polynucleotide or fusion polypeptide-expressing APC may be CD4+ and/or CD8+. Protein-specific T cells may be expanded using standard techniques. Within preferred embodiments, the T cells are derived from a patient, a related donor or an unrelated donor, and are administered to the patient following stimulation and expansion.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

In another aspect of this invention, vaccines and pharmaceutical compositions are provided for the prevention of Leishmania infection, and complications thereof, in a mammal, preferably a human or dog. Pharmaceutical compositions generally comprise one or more fusion polypeptides as described herein, and a physiologically acceptable carrier. The vaccines comprise one or more of the above fusion polypeptides and an adjuvant, for enhancement of the immune response.

Routes and frequency of administration and fusion polypeptide doses will vary from individual to individual and may parallel those currently being used in immunization against other protozoan infections. In general, the pharmaceutical compositions and vaccines may be administered by injection (e.g., intramuscular, intravenous or subcutaneous), intranasally (e.g., by aspiration) or orally. Between 1 and 4 doses may be administered for a 2-6 week period. Preferably, two doses are administered, with the second dose 2-4 weeks later than the first. A suitable dose is an amount of fusion polypeptide that is effective to raise antibodies in a treated mammal that are sufficient to protect the mammal from Leishmania infection for a period of time. In general, the amount of fusion polypeptide present in a dose ranges from about 1 pg to about 100 mg per kg of host, typically from about 10 pg to about 1 mg, and preferably from about 100 pg to about 1 µg. Suitable dose sizes will vary with the size of the animal, but will typically range from about 0.01 mL to about 5 mL for 10-60 kg animal.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune response, such as lipid A, Bordella pertussis or Mycobacterium tuberculosis. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

EXAMPLES

Example 1

Cloning and Expression of Leishmania Fusion Polypeptide

The present invention relates to a synthetic gene construct, referred to as K28, comprising sequences derived from 3 Leishmania donovani genes. The synthetic gene comprises partial DNA sequences of the K26 and K39 genes and the complete DNA sequences of the K9 gene. Additionally, the synthetic gene comprises a nine amino acid N-terminal motif, which includes 6 histidines (e.g., a 6×HIS epitope tag). The synthetic DNA construct was cloned into the NdeI/XhoI site of plasmid pCRX2.1 in order to express the fusion protein of this gene. The synthetic gene contains three 14 amino acid repeats of K26 encoded by SEQ ID NO: 1, two 39 amino acid repeats of K39 encoded by SEQ ID NO: 2, and the complete open reading frame for the K9 gene encoded by SEQ ID NO: 3. This fusion construct was designed to improve the diagnostic potential of each of these single proteins into one molecule and offers a broader coverage, increased sensitivity and reduced costs in terms of manufacturing a single protein instead of all three.

Example 2

Detection of Asymptomatic and Sub-Clinical Visceral Leishmania Infections in Humans Using a K28 Polypeptide This Example illustrates the increased detection sensitivity of Leishmania infection in humans using a fusion polypeptide of the invention, prepared as described in Example 1, in an ELISA format.

The ELISA assays were performed as follows. Three series of Polysorp 96 well plates (Nunc, Rochester, N.Y.) were each coated with 2 µg/ml of a different recombinant antigen in bicarbonate buffer overnight at 4° C. and blocked for 2 hours at room temperature with PBST with 1% (w/v) BSA on a plate shaker. Sera were diluted appropriately to 1/200 in PBST with 0.1% BSA, added to each well and plates were incubated at room temperature for 2 hours with shaking.

Plates were washed with PBST with 0.1% BSA and then HRP conjugated IgG immunoglobulin (Sigma, St. Louis, Mo.), diluted 1:10000 in PBST and 0.1% BSA, was added to each well and incubated at room temperature for 60 minutes with shaking. After washing, plates were developed with peroxidase color substrate (KPL, Baltimore Md.) with reaction quenched by addition of 1N $H_2SO_4$ after 10 minutes. The corrected optical density of each well at 450-570 nm was read using a VERSAmax® microplate reader (Molecular Devices, Sunnyvale, Calif.). The cut-off value was determined for each test by calculating the mean of the Enzyme Conjugate negative controls plus three standard deviations (EC).

Venezuelan individuals with visceral leishmaniasis (VL) were identified based on serology (e.g., IFAT or IHA immunofluorescence or hemaglutination), clinical symptoms (e.g., malaise, diarrhea, splenomegaly and hepatomegaly) and whole lysate ELISA. Of 52 serum samples from patients with VL, 94% tested positive using the above assay. However, the K28 antigen test displayed significantly higher ODs in 33% of the weak or marginally detected samples using the K39 antigen alone. In addition, 3 samples that were initially characterized as negative using the K39 assay were reliably detected using the K28 antigen test.

Figure 2:
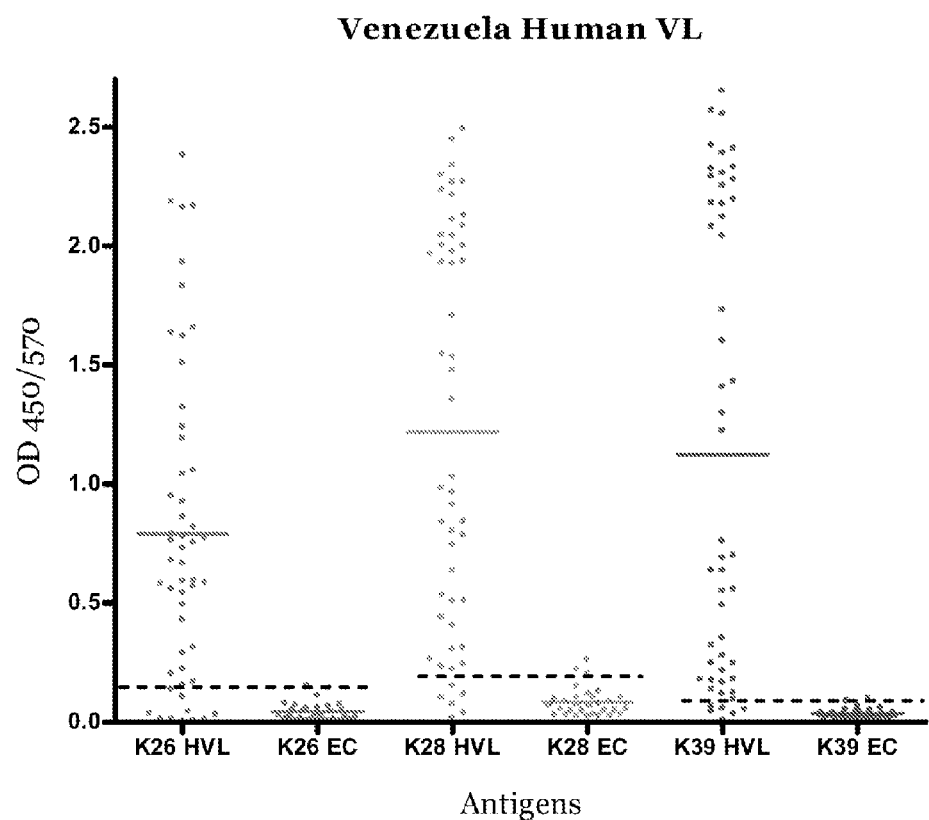
FIG. 2 shows a comparison of the ability of K28, K39, and K9 antigens to detect VL in the serum of human patients from Venezuela.

These results are depicted in FIG. 2, which show the distribution of absorbance values at 450-570 nm for the 52 VL serum samples assayed with K26, K28, and K39. These results indicate that using K28 provides increased sensitivity over using K39 alone to detect asymptomatic or sub-clinical visceral leishmaniasis.

Example 3

Detection of Asymptomatic and Sub-Clinical Visceral *Leishmania* Infections in Canines Using a K28 Polypeptide This Example illustrates the increased detection sensitivity of *Leishmania* infection in canines using a fusion polypeptide of the invention, prepared as described in Example 1, in an ELISA format.

The ELISA assays were performed as described in Example 2, except that 4 different recombinant antigens were used. Four series of Polysorp 96 well plates were each coated with 2 μg/ml of either K9, K26, K28, or K39 recombinant antigens. Venezuelan canines with visceral leishmaniasis (VL) were identified based on serology (e.g., IFAT or IHA immunofluorescence or hemaglutination), clinical symptoms (e.g., malaise, diarrhea, splenomegaly and hepatomegaly) and whole lysate ELISA.

Figure 3:
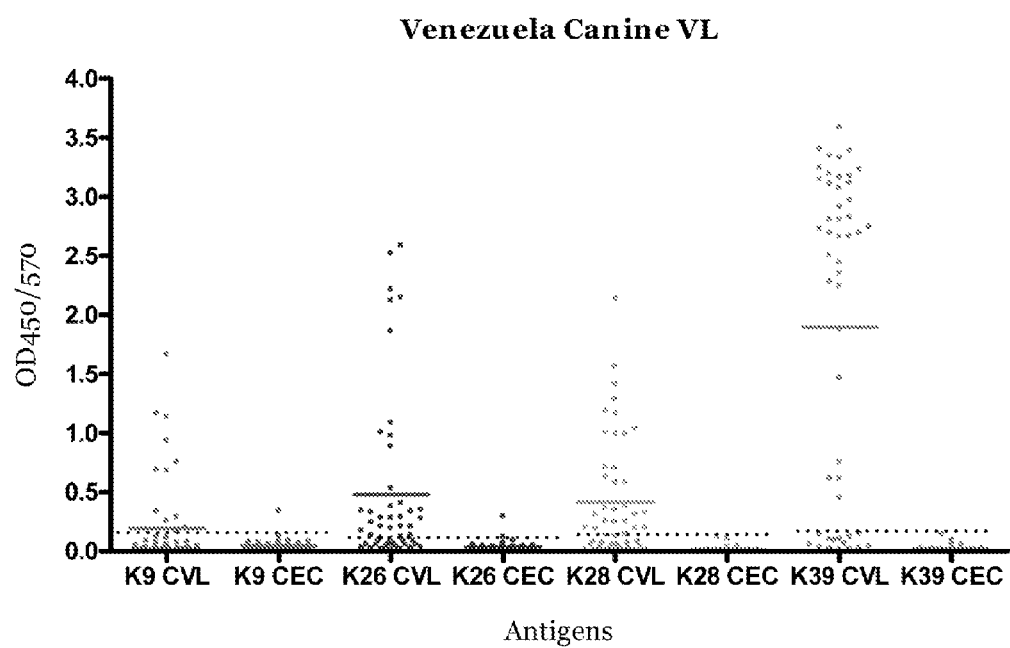
FIG. 3 shows a comparison of the ability of K9, K26, K28, and K39 antigens to detect VL in the serum of canines from Venezuela.

The results depicted in FIG. 3 show that K28 identified a significantly greater number of cases than either of the other three antigens used alone. This indicates that using K28 provides increased sensitivity in canines to detect asymptomatic or sub-clinical leishmaniasis, and moreover, K28 provides increased sensitivity of detection over using K9, K26, and K39 antigens alone.

Example 4

Detection of Visceral *Leishmania* Infections in Humans Using a K28 Polypeptide or a K39 Polypeptide in a Dual Path Rapid Test Format Compared to Direct Agllutination Assay This Example illustrates the increased detection sensitivity of *Leishmania* infection in humans using a fusion polypeptide of the invention (K28), prepared as described in Example 1, versus a single antigen (K39) in a dual path rapid test format, as compared to a direct agglutination assay (DAT) using sera from Sudan.

The dual path rapid test was performed essentially as described in U.S. Pat. No. 7,189,522, which is herein incorporated by reference in its entirety. Briefly, K28 or K39 was coated onto a strip of nitrocellulose. A drop of appropriately diluted human serum was added to the sample well in a test cartridge containing the antigen-impregnated nitrocellulose. Two drops of sample buffer were then added to the sample well and the sample was allowed to migrate by capillary action until the lines in the detection window of the test cartridge disappeared. Two drops of buffer were then added to the detection reagent well in the test cartridge to reconstitute immobilized detection reagent (colloidal gold-conjugated Staphylococcal protein A).

The detection reagent migrates by capillary flow to the detection window. If the sample contains antibodies to the test antigen, they bind to the immobilized antigen in the detection window where they will be visualized as two pink lines by binding of the detection reagent. A single pink line indicates that there is no antibody in the sample and that the detection reagent is bound to immobilized, control immunoglobulin (Ig) in the detection window. The absence of any pink lines is indicative of a defective test.

The DAT test was performed essentially as described by Sundar and Rai in Clin Diag Lab Immunol 9: 951-958, 2002.

The results of this analysis demonstated that K28 identified a significantly greater number of cases of human VL than did K39 alone. More specifically, K28 provided increased sensitivity in humans (66/69 samples, 95.6%) to detect visceral leishmaniasis versus K39 alone (61/69 samples, 88.4%) when employed in a dual path rapid test format. In addition, 4 patient samples with very low DAT titers (<3200) were correctly identified by the K28 rapid test, while only 2 of the 4 were correctly identified by the K39 rapid test.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheetare incorporated herein by reference, in their entirety. Aspects of the embodiments can be modified, if necessary to employ concepts of the various patents, applications and publications to provide yet further embodiments.

We claim:

1. A method for detecting asymptomatic or sub-clinical *Leishmania* infection in a biological sample comprising:
   (a) contacting a biological sample with a fusion polypeptide comprising *Leishmania* antigens K26, K39, and K9, wherein the *Leishmania* antigen K26 comprises a sequence having at least 95% identity to SEQ ID NO:5, the *Leishmania* antigen K39 comprises a sequence having at least 95% identity to SEQ ID NO:6, and the *Leishmania* antigen K9 comprises a sequence having at least 95% identity to SEQ ID NO:7 ; and
   (b) detecting in the biological sample the presence of antibodies that bind to the fusion polypeptide, thereby detecting asymptomatic or sub-clinical *Leishmania* infection in the biological sample.

2. The method of claim 1, wherein the fusion polypeptide comprises an amino acid sequence as set forth in 10-262 of SEQ ID NO: 8, or a sequence haying at least 95% identity thereto along its entire length.

3. The method of claim 2, wherein the fusion polypeptide further comprises an N-terminal amino acid sequence of MHHHHHHTS (SEQ ID NO: 21).

4. The method of claim 1, wherein the fusion polypeptide is bound to a solid support.

5. The method of claim 4, wherein the solid support comprises nitrocellulose, latex or a plastic material.

6. The method of claim 1, wherein the step of detecting comprises:
   (a) removing unbound sample from the solid support;
   (b) adding a detection reagent to the solid support; and
   (c) determining the level of detection reagent bound to the solid support, relative to a predetermined cutoff value.

7. The method of claim 6, wherein the detection reagent comprises a reporter group conjugated to a binding agent.

8. The method of claim 7 wherein the binding agent is selected from the group consisting of anti-immunoglobulin, Protein G, Protein A and lectins.

9. The method of claim 7 wherein the reporter group is selected from the group consisting of radioisotopes, fluorescent groups, luminescent groups, enzymes, biotin and dye particles.

10. The method of claim 1 wherein the biological sample is selected from the group consisting of sera, blood, and saliva.

* * * * *

SEQUENCE LISTING

<160> NUMBER OF SEQ ID NOS: 21

<210> SEQ ID NO 1
<211> LENGTH: 126
<212> TYPE: DNA
<213> ORGANISM: L. donovani

<400> SEQUENCE: 1

```
ccgaaggagg acggccatac acagaaaaat gacggcgatg cccctaagga ggacggccat    60
acacagaaaa atgacggcga tggcccgaag gaggacggcc atacacagaa aaatgacggc   120
gatggc                                                             126

<210> SEQ ID NO 2
<211> LENGTH: 234
<212> TYPE: DNA
<213> ORGANISM: L. donovani

<400> SEQUENCE: 2
cttgagcagc tgcttcgcga atccgaggag cgcgctgcgg agctggcgag tcagctggag    60
tccactactg ctgcgaagat gtcggcggag caggaccgcg agaacacgag gccacgcta    120 gagcagcagc ttcgtgactc cgaggagcgc gctgcggagc tggcgagcca gctggaggcc   180
actgctgctg cgaagtcgtc ggcggagcag gaccgcgaga cacgagggc cgcg          234

<210> SEQ ID NO 3
<211> LENGTH: 399
<212> TYPE: DNA
<213> ORGANISM: L. donovani

<400> SEQUENCE: 3
atgggaagtt cttgtacaaa ggactccgca aggagccccc agaagcgtgc tgataacatc    60
cataaaacca ctgaggccaa tcacagaggc gccgccgtgc ccccgaagca cgccggcggt   120
gcgatgaacg actctgcccc gaagaaggat ggccatacac agaaaaatga cggcgatggc   180
cctaaggagg atgaccatac acagaaaaat gacggcgatg cccctaagga ggatgaccat   240
gcgcacaacg acggcggtgg ccctaaggag gatgagaatc tgccgcaaaa cgatggggat   300
gcgcaggaga gaacgaaga tggacacaac gtggggggatg gagctaacga caatgaggat   360
ggtaacgatg atcagccgaa ggagcacgct gccggcaac                          399

<210> SEQ ID NO 4
<211> LENGTH: 804
<212> TYPE: DNA
<213> ORGANISM: Artificial Sequence
<220> FEATURE:
<223> OTHER INFORMATION: Polynucleotide sequence of a synthetic gene
      K28.

<400> SEQUENCE: 4
catatgcatc accatcacca tcacactagt ccgaaggagg acggccatac acagaaaaat    60
gacggcgatg cccctaagga ggacggccat acacagaaaa atgacggcga tggcccgaag   120
gaggacggcc atacacagaa aaatgacggc gatggccttg agcagctgct tcgcgaatcc   180
gaggagcgcg ctgcggagct ggcgagtcag ctggagtcca ctactgctgc gaagatgtcg   240
gcggagcagg accgcgagaa cacgagggcc acgctagagc agcagcttcg tgactccgag   300
gagcgcgctg cggagctggc gagccagctg gaggccactg ctgctgcgaa gtcgtcggcg   360
gagcaggacc gcgagaacac gagggccgcg atgggaagtt cttgtacaaa ggactccgca   420
aaggagcccc agaagcgtgc tgataacatc cataaaacca ctgaggccaa tcacagaggc   480
gccgccgtgc ccccgaagca cgccggcggt gcgatgaacg actctgcccc gaagaaggat   540
ggccatacac agaaaaatga cggcgatggc cctaaggagg atgaccatac acagaaaaat   600
gacggcgatg cccctaagga ggatgaccat gcgcacaacg acggcggtgg ccctaaggag   660
gatgagaatc tgccgcaaaa cgatggggat gcgcaggaga gaacgaaga tggacacaac   720
```

-continued

```
gtgggggatg agctaacga caatgaggat ggtaacgatg atcagccgaa ggagcacgct    780
gccggcaacg ctagctgact cgag                                          804
```

<210> SEQ ID NO 5
<211> LENGTH: 42
<212> TYPE: PRT
<213> ORGANISM: L. donovani

<400> SEQUENCE: 5

```
Pro Lys Glu Asp Gly His Thr Gln Lys Asn Asp Gly Asp Gly Pro Lys
1               5                   10                  15

Glu Asp Gly His Thr Gln Lys Asn Asp Gly Asp Gly Pro Lys Glu Asp
            20                  25                  30

Gly His Thr Gln Lys Asn Asp Gly Asp Gly
        35                  40
```

<210> SEQ ID NO 6
<211> LENGTH: 78
<212> TYPE: PRT
<213> ORGANISM: L. donovani

<400> SEQUENCE: 6

```
Leu Glu Gln Leu Leu Arg Glu Ser Glu Arg Ala Ala Glu Leu Ala
1               5                   10                  15

Ser Gln Leu Glu Ser Thr Thr Ala Ala Lys Met Ser Glu Gln Asp
            20                  25                  30

Arg Glu Asn Thr Arg Ala Thr Leu Glu Gln Gln Leu Arg Asp Ser Glu
            35                  40                  45

Glu Arg Ala Ala Glu Leu Ala Ser Gln Leu Glu Ala Thr Ala Ala Ala
        50                  55                  60

Lys Ser Ser Ala Glu Gln Asp Arg Glu Asn Thr Arg Ala Ala
65                  70                  75
```

<210> SEQ ID NO 7
<211> LENGTH: 133
<212> TYPE: PRT
<213> ORGANISM: L. donovani

<400> SEQUENCE: 7

```
Met Gly Ser Ser Cys Thr Lys Asp Ser Ala Lys Glu Pro Gln Lys Arg
1               5                   10                  15

Ala Asp Asn Ile His Lys Thr Thr Glu Ala Asn His Arg Gly Ala Ala
            20                  25                  30

Val Pro Pro Lys His Ala Gly Ala Met Asn Asp Ser Ala Pro Lys
            35                  40                  45

Lys Asp Gly His Thr Gln Lys Asn Asp Gly Asp Gly Pro Lys Glu Asp
        50                  55                  60

Asp His Thr Gln Lys Asn Asp Gly Asp Gly Pro Lys Glu Asp His
65                  70                  75                  80

Ala His Asn Asp Gly Gly Pro Lys Glu Glu Asn Leu Pro Gln
            85                  90                  95

Asn Asp Gly Asp Ala Gln Glu Lys Asn Glu Gly His Asn Val Gly
            100                 105                 110

Asp Gly Ala Asn Asp Asn Glu Asp Gly Asn Asp Gln Pro Lys Glu
        115                 120                 125

His Ala Ala Gly Asn
        130
```

```
<210> SEQ ID NO 8
<211> LENGTH: 264
<212> TYPE: PRT
<213> ORGANISM: Artificial Sequence
<220> FEATURE:
<223> OTHER INFORMATION: Amino acid sequence of the synthetic gene K28.

<400> SEQUENCE: 8

Met His His His His His His Thr Ser Pro Lys Glu Asp Gly His Thr
1               5                   10                  15

Gln Lys Asn Asp Gly Asp Gly Pro Lys Glu Asp Gly His Thr Gln Lys
            20                  25                  30

Asn Asp Gly Asp Gly Pro Lys Glu Asp Gly His Thr Gln Lys Asn Asp
        35                  40                  45

Gly Asp Gly Leu Glu Gln Leu Leu Arg Glu Ser Glu Glu Arg Ala Ala
    50                  55                  60

Glu Leu Ala Ser Gln Leu Glu Ser Thr Thr Ala Ala Lys Met Ser Ala
65                  70                  75                  80

Glu Gln Asp Arg Glu Asn Thr Arg Ala Thr Leu Glu Gln Leu Arg
                85                  90                  95

Asp Ser Glu Glu Arg Ala Ala Glu Leu Ala Ser Gln Leu Glu Ala Thr
            100                 105                 110

Ala Ala Ala Lys Ser Ser Ala Glu Gln Asp Arg Glu Asn Thr Arg Ala
        115                 120                 125

Ala Met Gly Ser Ser Cys Thr Lys Asp Ser Ala Lys Glu Pro Gln Lys
    130                 135                 140

Arg Ala Asp Asn Ile His Lys Thr Thr Glu Ala Asn His Arg Gly Ala
145                 150                 155                 160

Ala Val Pro Pro Lys His Ala Gly Gly Ala Met Asn Asp Ser Ala Pro
                165                 170                 175

Lys Lys Asp Gly His Thr Gln Lys Asn Asp Gly Asp Gly Pro Lys Glu
            180                 185                 190

Asp Asp His Thr Gln Lys Asn Asp Gly Asp Gly Pro Lys Glu Asp Asp
        195                 200                 205

His Ala His Asn Asp Gly Gly Pro Lys Glu Asp Glu Asn Leu Pro
    210                 215                 220

Gln Asn Asp Gly Asp Ala Gln Glu Lys Asn Glu Asp Gly His Asn Val
225                 230                 235                 240

Gly Asp Gly Ala Asn Asp Asn Glu Asp Gly Asn Asp Gln Pro Lys
                245                 250                 255

Glu His Ala Ala Gly Asn Ala Ser
            260

<210> SEQ ID NO 9
<211> LENGTH: 14
<212> TYPE: PRT
<213> ORGANISM: L. donovani

<400> SEQUENCE: 9

Pro Lys Glu Asp Gly His Thr Gln Lys Asn Asp Gly Asp Gly
1               5                   10

<210> SEQ ID NO 10
<211> LENGTH: 39
<212> TYPE: PRT
<213> ORGANISM: L. donovani

<400> SEQUENCE: 10
```

```
Leu Glu Gln Leu Leu Arg Glu Ser Glu Glu Arg Ala Ala Glu Leu Ala
1               5                   10                  15

Ser Gln Leu Glu Ser Thr Thr Ala Ala Lys Met Ser Ala Glu Gln Asp
            20                  25                  30

Arg Glu Asn Thr Arg Ala Thr
            35
```

```
<210> SEQ ID NO 11
<211> LENGTH: 39
<212> TYPE: PRT
<213> ORGANISM: L. donovani

<400> SEQUENCE: 11

Leu Glu Gln Gln Leu Arg Asp Ser Glu Glu Arg Ala Ala Glu Leu Ala
1               5                   10                  15

Ser Gln Leu Glu Ala Thr Ala Ala Ala Lys Ser Ser Ala Glu Gln Asp
            20                  25                  30

Arg Glu Asn Thr Arg Ala Ala
            35
```

```
<210> SEQ ID NO 12
<211> LENGTH: 42
<212> TYPE: DNA
<213> ORGANISM: L. donovani

<400> SEQUENCE: 12
ccgaaggagg acggccatac acagaaaaat gacggcgatg gc                    42
```

```
<210> SEQ ID NO 13
<211> LENGTH: 42
<212> TYPE: DNA
<213> ORGANISM: L. donovani

<400> SEQUENCE: 13
cctaaggagg acggccatac acagaaaaat gacggcgatg gc                    42
```

```
<210> SEQ ID NO 14
<211> LENGTH: 117
<212> TYPE: DNA
<213> ORGANISM: L. donovani

<400> SEQUENCE: 14
cttgagcagc tgcttcgcga atccgaggag cgcgctgcgg agctggcgag tcagctggag    60
tccactactg ctgcgaagat gtcggcggag caggaccgcg agaacacgag ggccacg      117
```

```
<210> SEQ ID NO 15
<211> LENGTH: 117
<212> TYPE: DNA
<213> ORGANISM: L. donovani

<400> SEQUENCE: 15
ctagagcagc agcttcgtga ctccgaggag cgcgctgcgg agctggcgag ccagctggag    60
gccactgctg ctgcgaagtc gtcggcggag caggaccgcg agaacacgag ggccgcg      117
```

```
<210> SEQ ID NO 16
<211> LENGTH: 1206
<212> TYPE: DNA
<213> ORGANISM: L. donovani

<400> SEQUENCE: 16
```

```
atgggaactt cttgtacaaa ggactccgca aaggagcccc agaagcgtgc tgataacatc      60
cataaaacca ctgaggccaa tcacggaggc gccactggtg tgcccccgaa gcacaccggc     120
agtgcgatga acgactctgc cccgaaggag gacggccata cacagaaaaa tgacggcgat     180
ggccctaagg aggacggcca tacacagaaa aatgacggcg atggccccgaa ggaggacggc     240 catacacaga aaaatgacgg cgatggccct aaggaggacg ccatacaca gaaaaatgac     300 ggcgatggcc cgaaggagga cggccataca cagaaaaatg acggcgatgg ccctaaggag     360
gacggccata cacagaaaaa tgacggcgat ggcccgaagg aggacggcca tacacagaaa     420
aatgacggcg atggccctaa ggaggacggc catacacaga aaaatgacgg cgatggcccg     480
aaggaggacg ccatacaca gaaaaatgac ggcgatggcc taaggagga cggccataca     540 cagaaaaatg acggcgatgg cccgaaggag gacggccata cacagaaaaa tgacggcgat     600
ggcccgaagg aggacggcca tacacagaaa aatgacggcg atggccctaa ggaggacggc     660
catacacaga aaaatgacgg cgatggcccg aaggaggacg ccatacaca gaaaaatgac     720 ggcgatggcc taaggagga cggccataca cagaaaaatg acggcgatgg cccgaaggag     780
gacggccata cacagaaaaa tgacggcgat ggccctaagg aggacggcca tacacagaaa     840
aatgacggcg atgcccgaa ggaggacggc catacacaga aaaatgacgg cgatggcccct     900 aaggaggacg ccatacaca gaaaaatgac ggcgatggcc cgaaggagga cggccataca     960
cagaaaaatg acggcgatgg ccctaaggag gacggccata cacagaaaaa tgacggcgat    1020
ggcccgaagg aggacggcca tacacagaaa aatgacggcg atggccctaa ggagggtgag    1080
aatctgcagc aaaacgatgg ggatgcgcag gagaagaacg aagatggaca caacgtgggg    1140
gatggagcta acggcaatga ggatggtaac gatgatcagc cgaaggagca cgctgccggc    1200
aactag                                                              1206
```

<210> SEQ ID NO 17
<211> LENGTH: 9831
<212> TYPE: DNA
<213> ORGANISM: L. donovani

<400> SEQUENCE: 17

```
atgcacccttt ccactgtgcg gcgtgaggcg gagcgggtga aggtgtcggt gcgcgtgcgc      60
cccctaaacg aacgtgaaaa caatgccccg gaagggacga agtgaccgt tgcggcgaaa     120 caggcggccg ccgtggtgac ggtcaaggtc ctgggaggca gcaacaacag cggcgccgcc     180
gagtcgatgg ggactgcaag gcgggtagcg caggactttc agttcgacca cgtgttctgg     240
tctgtggaga cgccggacgc gtgcggcgcg accccccgcga cgcaggcaga cgtgttccgg     300
acgatcgggt acccgctggt gcagcacgcg ttcgacgggt tcaactcgtg cttgttttgcg     360 tacgggcaga cagggagcgg gaagacgtac acgatgatgg gcgcggacgt gagcgtgctt     420
agtggtgagg gcaacggcgt gacgccgcgg atctgcctgg agatctttgc gcggaaggcg     480
agcgtggagg cgcaggggca ctcgcggtgg atcgtgagc tggggtacgt ggaggtgtac     540
aacgagcgcg tgtcggacct gcttgggaag cggaagaagg gtgtgaaggg cggcggcgag     600
gaggtgtacg tggacgtgcg cgagcacccg agccgcggcg tgttcctgga ggggcagcgg     660
ctggtggagg ttgggagcct ggacgatgtt gtgcggctga tcgagatcgg caacggcgtg     720
cggcacaccg cttcgacgaa gatgaacgac cggagcagcc ggagccacgc gatcatcatg     780
ctgctgctgc gcaggagcg gacgatgacg acgaagagcg gggagacgat ccgtactgcc     840
ggcaagagca gccgcatgaa ccttgtggac cttgcggggt ctgagcgcgt ggcgcagtcg     900
```

```
caggtggagg ggcagcagtt caaggaggcg acgcacatca acctgtcgct gacgacgctc    960
gggcgcgtga tcgacgtgct cgcggacatg gcgacgaagg gtgcgaaggc gcagtacagc   1020
gttgcgccgt tccgcgactc gaagctgacg ttcatcctga aggactcgct tggcgggaac   1080
tcgaagacgt tcatgatcgc gactgtgagc ccgagcgcgc tgaactacga ggagacgctg   1140
agcacgctgc ggtacgcgtc gcgcgcgcgc gacattgtga atgttgcgca ggtgaacgag   1200
gacccgcgcg cacggcggat ccgcgagctg gaggagcaga tggaggacat gcggcaggcg   1260
atggctggcg gcgaccccgc gtacgtgtct gagctgaaga agaagcttgc gctgctggag   1320
tcggaggcgc agaagcgtgc ggcggacctg caggcgctgg agggagcg ggagcacaac    1380 caggtgcagg agcggctgct gcgcgcgacg gaggcggaga gagcgagct ggagtcgcgt    1440 gcggctgcgc tgcaggagga gatggccgcg actcgacggc aggcggacaa gatgcaggcg   1500
ctgaacctgc ggctgaagga gagcaggcg cgcaaggagc gcgagctgct gaaagagatg     1560
gcgaagaagg acgccgcgct ctcgaaggtt cggcgacgca agacgccga gatagcaagc     1620 gagcgcgaga agctggagtc gaccgtggcg cagctggagc gtgagcagcg cgagcgcgag   1680
gtggctctgg acgcattgca gacgcaccag agaaagctgc aggaagcgct cgagagctct   1740
gagcggacag ccgcggaaag ggaccagctg cttcagcagc taacagagct tcagtctgag   1800
cgtacgcagc tatcacaggt tgtgaccgac cgcgagcggc ttacacgcga cttgcagcgt   1860
attcagtacg agtacgggga aaccgagctc gcgcgagacg tggcgctgtg cgccgcgcag   1920
gagatggagg cgcgctacca cgctgctgtg tttcacctgc aaacgctcct ggagctcgca   1980
accgagtggg aggacgcact ccgcgagcgt gcgcttgcag agcgtgacga agccgctgca   2040
gccgaacttg atgccgcagc ctctacttcc caaaacgcac gtgaaagcgc ctccgagcgg   2100
ctaaccagcc ttgagcagct gcttcgcgaa tccgaggagc gcgctgcgga gctggcgagt   2160
cagctggagt ccactactgc tgcgaagatg tcggcggagc aggaccgcga gaacacgagg   2220
gccacgctag agcagcagct tcgtgactcc gaggagcgcg ctgcggagct ggcgagccag   2280
ctggaggcca ctgctgctgc gaagtcgtcg gcggagcagg accgcgagaa cacgagggcc   2340
gcgttggagc agcagcttcg tgactccgag gagcgcgctg cggagctggc gagtcagctg   2400
gagtccacta ctgctgcgaa gacgtcggcg gagcaggacc gcgagaacac gagggccacg   2460
ctagagcagc agcttcgtga ctccgaggag cgcgctgcgg agctggcgag tcagctggag   2520
tccactactg ctgcgaagat gtcagcggag caggaccgcg agaacacgag ggccgcgcta   2580
gagcagcagc ttctcgaatc cgaggagcgc gctgcggagc tgaaggccga gctagaggcc   2640
actgctgctg cgaagtcgtc ggcggagcag gaccgcgaga acacgagggc gcgttggag    2700 cagcagcttc gtgactccga ggagcgcgct cggagctgg cgagtcagct ggagtccact    2760
actgctgcga agacgtcggc ggagcaggac cgcgagaaca cgagggccac gctagagcag   2820
cagcttcgtg actccgagga gcgcgctgcg gagctggcga gtcagctgga gtccactact   2880
gctgcgaaga tgtcggcgga gcaggaccgc gagaacacga gggccacgct agagcagcag   2940
cttcgtgact ccgaggagcg cgctgcggag ctggcgagtc agctggagtc cactactgct   3000
gcgaagatgt cggcggagca ggaccgcgag aacacgaggg ccacgctaga gcagcagctt   3060
cgtgactccg aggagcgcgc tgcggagctg gcgagtcagc tggagtccac tactgctgcg   3120
aagatgtcag cggagcagga ccgcgagaac acgagggccg cgctagagca gcagcttctc   3180
gaatccgagg agcgcgctgc ggagctgaag gccgagctag aggccactgc tgctgcgaag   3240
```

```
tcgtcggcgg agcaggaccg cgagaacacg agggccacgc tagagcagca gcttcgtgac     3300
tccgaggagc gcgctgcgga gctggcgagc cagctggagg ccactgctgc tgcgaagtcg     3360
tcggcggagc aggaccgcga gaacacgagg gccgcgttgg agcagcagct tcgtgactcc     3420
gaggagcgcg ctggggagct ggcgagccag ctggaggcca ctgctgctgc gaagtcgtcg     3480
gcggagcagg accgcgagaa cacgagggcc gcgttggagc agcagcttct cgaatccgag     3540
gcgcgcgctg cggagctggc gagccagctg gaggccactg ctgctgcgaa gtcgtcggcg     3600
gagcaggacc gcgagaacac gagggccgcg ttggagcagc agcttcgcga atccgaggcg     3660
cgcgctgggg agctggcgag ccagctggag gccactgctg ctgcgaagat gtcagcggag     3720
caggaccgcg agaacacgag ggccgcgttg gagcagcagc ttcgcgaatc cgaggagcgc     3780
gctgcgagcc tggcgagcca gctggaggcc actgctgctg cgaagtcgtc ggcggagcag     3840
gaccgcgaga cacgagggc cgcgttggag cagcagcttc gcgaatccga ggcgcgcgct     3900
gcggagctgg cgagccagct ggaggccact gctgctgcga agtcgtcggc ggagcaggac     3960
cgcgagaaca cgagggccgc gttggagcag cagcttcgcg aatccgaggc gcgcgctgcg     4020
gagctggcga gccagctgga ggccactgct gctgcgaaga cgtcggcgga gcaggaccgc     4080
gagaacacga gggccgcgtt ggagcagcag cttcgcgaat ccgaggagcg cgctgcggag     4140
ctggcgagcc agctggaggc cactgctgct gcgaagatgt cggcggagca ggaccgcgag     4200
aacacgaggg ccacgctaga gcagcagctt ctcgaatccg aggagcgcgc tgcggagctg     4260
gcgagccagc tggaggccac tgctgctgcg aagatgtcgg cggagcagga ccgcgagaac     4320
acgagggcca cgctagagca gcagcttctc gaatccgagg agcgcgctgc ggagctggcg     4380
agccagctgg aggccactgc tgctgcgaag tcgtcggcgg agcaggaccg cgagaacacg     4440
agggccgcgt tggagcagca gcttcgggaa tccgaggcgc gcgctgcgga gctggcgagc     4500
cagctggagg ccactgctgc tgcgaagacg tcggcggagc aggaccgcga gaacacgagg     4560
gccacgctag agcagcagct tcgcgaatcc gaggcgcgcg ctggggagct ggcgagccag     4620
ctggaggcca ctgctgctgc gaagtcgtcg gcggagcagg accgcgagaa cacgagggcc     4680
gcgttggagc agcagcttcg ggaatccgag gagcgcgctg cggagctgat gcggaagtta     4740
gaggcgactg ctgctgcgaa gtcgtcggta gagcaggacc gtgagagcat gaaggtagcg     4800
cttgaggcgc gcaccgcgga gctggcttct cgattgaagg cgacggctgc tgcgaagacg     4860
tcggccgagc aggagcgaga taggacaagg gctacctttg aggagaggct aagagttgct     4920
gaagtgcgcg ctgtgcagct ggcgagtcag ctggaggcca ctgctgctgc gaagtcgtcg     4980
gtggagcagg accgcgaaaa gacgaggaca gctctggaag cgcgcgttgc ggagctggcg     5040
agcaagctgg aggccactgc tgctgcgaag gctttggtag agcaggaccg cgagaacacg     5100
agggccactt tagaggagcg actccggktt gctgaggtgc gggctgcgga gctggcagcg     5160
cagctggagg ccactgctgc tgcgaagtcg tcggtggagc aggaccgcga aaagacgagg     5220
acggctctgg aagcgcgcgt tgcggagctg gcgagcaagc tggaggccac tgctgcggcg     5280
aagacttcgg cggagcagga ccgcgagagc acgagggcca ccttgaagga gcggcttcgg     5340
attgcggagg tgcgcgctgc ggagctggca acccagttgg aggcgacttc ggctgcgaag     5400
acgtcggtgg agcaggaccg cgagagaacg agggcggctc tggaggcgcg cgttgcggag     5460
ctggcgagca gctggagtc gacgcggct gcgaaggcct tggttgagca ggaccgcgag     5520
agcacgaggg ccaccttgga ggagcggctt cggattgcgg aggcgcgcgc tgcggaactt     5580
gccattgagt tggatgccac tgctgctgcg aaggcttcga tggaacatga ccgcgagagc     5640
```

```
acgagggcca ctttagagga gcggcttcgg attgcggagg tgcgcggagc ggaactggca    5700
agtcagctag aggccactgc tgctgcaaaa gcgttgttgg agcaggaccg ggagagaacg    5760
agggcggctc tggaggctcg agctgcggag ctggcgagca agctggaggc cactgctgct    5820
gcgaagatgt cggcggagca ggaccgcgag agaaccaggg cggccataga ggagcagctt    5880
cggctcgctg aggtgcgcgc tgcggagctg gcgagccagc tggaggccac tgctgctgca    5940
aaagcgttgt tggagcagga ccgcgagaga acgagggcgg ctctggaagg ccgcgctgcg    6000
gagctggcgc gaaagctgga ggccactgct attgccaaga cggcggtgga acaggaccgg    6060
gaaagcacga gggccacctt ggaggagcgc ttgcgcggtg ctgaggtgcg cgttgcggag    6120
ctggcgagtc agctggaggc cactgctgct gcgaagacgt cggcggagca ggagcgtgcg    6180
aacactaggg cggcgttgga ggcccgcgct gcggagctgg cgagcaagct ggaggcgact    6240
gctgctgcga gttcgcggt ggagcaggac cgtgagagga cgagggccac cttggaggag    6300
cgcttgcgcg gtgctgaggt gcgcgctgcg gagctggcgc gcaagctgga ggctactgct    6360
gctgcgaagg cttcgatgga acatgatcgc gagagcacga gggcggcttt ggaagagcgg    6420
ttgcgggggg cggaggttcg tgctgcggag ctggcgagca agcttgaggc aactgcggct    6480
gcgaaggccg cagtggagca ggaccgcgag aggactcggg cgacctttga aaagcagctt    6540
cgtgactccg aggcgcgggt tgcggagctt tcagggcagc tagaggccac tgctgctgcg    6600
aagacgtcgg cggagcagga ccgcgagaac acgaaggctg ctctgcaggc gcgcgctgcg    6660
gagctgaagg cccagttgga gtccactgct gctgcgaaga tgtcagcgga gcaggaccgc    6720
gagaacacga gggccgcgtt ggagcagcgg cttcgtgaat ccgaggagca cgctgcggag    6780
ctgaaggccc agctggagtc cactgctgct gcgaagacgt cggcggacca ggaccgcgag    6840
aggatgaggg tcgcgctgca ggagcggctg cgcgtcgctg agttgcgcgc tgcggagctg    6900
gcgagtcagc tggaggccac tgttgccgcg aagacgtcgg cggagcagga ccgcgagaac    6960
acgagggcca cgctagagca gcagcttcgc gaatccgagg cgcgcgctgc ggagctggcg    7020
agccagctgg aggccactgc tgctgcgaag tcgtcggcgg agcaggaccg cgagaacaca    7080
aaggctgctc tgcaggcgcg cgctgcggag ctggcgagcc agctggagtc cactgctgct    7140
gcgaagatgt cagcggagca ggaccgcgag aacacgaggg ccacgctaga gcagcagctt    7200
cgcgaatccg aggcgcgcgc tgcagagctg gcgagtcagc tggagtccac tgctgctgcg    7260
aagacgtcgg cggagcagga ccgcgagaac acgagggcca cgctagagca gcagcttcgc    7320
gaatccgagg cgcgcgctgc ggagctggcg agccagctgg aggccactgc tgctgcgaag    7380
tcgtcggcgg agcaggaccg cgagaacaca aaggctgctc tgcaggcgcg cgctgcggag    7440
ctggcgagcc agctggagtc cactgctgct gcgaagatgt cagcggagca ggaccgcgag    7500
aacacgaggg ctgcgttgga gcagcggctt cgcgaatccg aggagcacgc tgcggagctg    7560
gcgagccagc tggaggccac tgctgctgcg aagtcgtcgg cggagcagga ccgcgagaac    7620
acgagggcca cgctagagca gcagcttcgc gactccgaga cgcgcgctgc ggagctggcg    7680
agtcagctgg agtccactgc tgctgcgaag acgtcggcgg agcaggaccg cgagaacacg    7740
agggccgcgt tggagcagcg gcttcgcgaa tccgaggcgc gcgctgcgga gctgaaggcc    7800
gagctggagg ccactgctgc cgcgaagacg tcggcggagc aggaccgcga gaacacgagg    7860
gccgcgttgg agcagcggct tcgcgaatcc gaggcgcgcg ctggggagct gaaggccgag    7920
ctggaggcca ctactgctgc gaagacgtcg gcggagcagg accgcgagaa cacgagggcc    7980
```

```
acgctagagc agcagcttcg cgactccgag gagcgcgctg cggagctggc gagccagctg     8040
gaggccactg ctgctgcgaa gtcgtcggcg gagcaggacc gcgagaacac gagggccacg     8100
ctagagcagc agcttcgcga atccgaggcg cgcgctgggg agctggcgag ccagctggag     8160
gccactgctg ctgcgaagtc gtcggcggag caggaccgcg agaacacgag gctgctctg      8220 caggcgcgcg ctgcggagct gaaggccgag ctggaggcca ctgctgctgc gaagacgtcg     8280
gcggagcagg accgcgagag gatgagggtc acgttggagg agcggcttcg cgtcgctgag     8340
ttgcgcgctg cggagctgac gggagtgctg gaggccactg ctgctgcgaa gacgtcggcg     8400
gagcaggatc gtgagaggac gaggaccacg ttgcaggagc agcttcgcga atccgaggcg     8460
cgcgctgcgg agctgaaggc cgagctggag gccactgctg ctgcgaagtc gtcggcggag     8520
caggaccgcg agaacacgag gctgctctg gaggagaagc taaggggcac cgaggcgcgc      8580
gctgcggagc tggaggcccg cctaaaggct atcgctgcga caaaggcatc gatcgagcag     8640
gagagggaga gctcgagggc ttctctggag gaaaggctaa ggggctctga ggcgcgcgct     8700
gcggagctgg ctgctcggct aaaggctgct gctgctgcga gacgtcggc ggagcaggag      8760 cgtgagaaca cgagggtgac gttggagcag cagcttcgcg aatccgagaa gcgcgctgcg     8820
gagctggcga gtcagctgga gtccactgct gctgcgaaga cgtcggcgga gcaggaccgc     8880
gagaacacga gggtcacgtt ggggcagcag cttcgcgaat ccgaggcgcg cgctgcggag     8940
ctgaaggccg agctggaggc cgctgctgct gcgaagtcgt cggcggagca ggaccgcgag     9000
aacacgaggg ctgctctgga ggagaagcta aggggcaccg aggcgcgcgc tgcggagctg     9060
gcggcccgcc taaaggctat tgctgcgatg aaggcgtcaa tggtcagga gcgggaaagc      9120 gcgagggatg ctctggagga aaagctaagg ggctctgagg cgcgcgctgc ggagctggct     9180
gctcggctaa aggctgctgc tgctgcgaag acgtcggcgg agcaggagcg tgagaacacg     9240
agggtgacgt tggagcagca gcttcgcgaa tccgaggagc gcgctgcgga gctggcgagt     9300
cagctggagg ccgctgctgc tgcgaagtcg tcggcggagc aggaccgcga gaacacgagg     9360
gctgctctgg aggagaagct aagagactcc gaggagcgcg ctgcggagct gggaacccgt     9420
gtaaaggcta gttctgcggc gaaggctttg gcggagcagg agcgggacag gataagggct     9480
gccctggagg agaagttgcg tgattcggag gcgcgcgctg cggagctgac gaccaagctg     9540
gaggccactg ttgctgcgaa gtcgtcggcg gagcaggagc gggaaaatat aaaggtggct     9600
ttagaggaag aattggttga tgcaagggcg aaattggctg gaatggaggc gtcgttgaag     9660
gaatcgaagt tggagtttga aggtcgtgtc ggggagcttg aaggagagtg cgagaagctg     9720
aggaatgata aggtcaggta tgcgaaaaag gttcaatcgc ttgagtatca gatgcgcatc     9780
gatgaggctc gactgaaggc gcgtcgtgat gcggttcatc gaaaggagtg a              9831
```

<210> SEQ ID NO 18
<211> LENGTH: 402
<212> TYPE: DNA
<213> ORGANISM: L. donovani

<400> SEQUENCE: 18

```
atgggaagtt cttgtacaaa ggactccgca aaggagcccc agaagcgtgc tgataacatc       60
cataaaacca ctgaggccaa tcacagaggc gccgccgtgc cccgaagca cgccggcggt       120 gcgatgaacg actctgcccc gaagaaggat ggccatacac agaaaaatga cggcgatggc       180
cctaaggagg atgaccatac acagaaaaat gacggcgatg cccttaagga ggatgaccat       240
gcgcacaacg acggcggtgg ccctaaggag gatgagaatc tgccgcaaaa cgatggggat       300
```

```
gcgcaggaga agaacgaaga tggacacaac gtgggggatg gagctaacga caatgaggat    360
ggtaacgatg atcagccgaa ggagcacgct gccggcaact ag                      402
```

<210> SEQ ID NO 19
<211> LENGTH: 401
<212> TYPE: PRT
<213> ORGANISM: L. donovani

<400> SEQUENCE: 19

```
Met Gly Thr Ser Cys Thr Lys Asp Ser Ala Lys Glu Pro Gln Lys Arg
1               5                   10                  15

Ala Asp Asn Ile His Lys Thr Thr Glu Ala Asn His Gly Gly Ala Thr
            20                  25                  30

Gly Val Pro Pro Lys His Thr Gly Ser Ala Met Asn Asp Ser Ala Pro
        35                  40                  45

Lys Glu Asp Gly His Thr Gln Lys Asn Asp Gly Asp Gly Pro Lys Glu
    50                  55                  60

Asp Gly His Thr Gln Lys Asn Asp Gly Asp Gly Pro Lys Glu Asp Gly
65                  70                  75                  80

His Thr Gln Lys Asn Asp Gly Asp Gly Pro Lys Glu Asp Gly His Thr
                85                  90                  95

Gln Lys Asn Asp Gly Asp Gly Pro Lys Glu Asp Gly His Thr Gln Lys
            100                 105                 110

Asn Asp Gly Asp Gly Pro Lys Glu Asp Gly His Thr Gln Lys Asn Asp
        115                 120                 125

Gly Asp Gly Pro Lys Glu Asp Gly His Thr Gln Lys Asn Asp Gly Asp
    130                 135                 140

Gly Pro Lys Glu Asp Gly His Thr Gln Lys Asn Asp Gly Asp Gly Pro
145                 150                 155                 160

Lys Glu Asp Gly His Thr Gln Lys Asn Asp Gly Asp Gly Pro Lys Glu
                165                 170                 175

Asp Gly His Thr Gln Lys Asn Asp Gly Asp Gly Pro Lys Glu Asp Gly
            180                 185                 190

His Thr Gln Lys Asn Asp Gly Asp Gly Pro Lys Glu Asp Gly His Thr
        195                 200                 205

Gln Lys Asn Asp Gly Asp Gly Pro Lys Glu Asp Gly His Thr Gln Lys
    210                 215                 220

Asn Asp Gly Asp Gly Pro Lys Glu Asp Gly His Thr Gln Lys Asn Asp
225                 230                 235                 240

Gly Asp Gly Pro Lys Glu Asp Gly His Thr Gln Lys Asn Asp Gly Asp
                245                 250                 255

Gly Pro Lys Glu Asp Gly His Thr Gln Lys Asn Asp Gly Asp Gly Pro
            260                 265                 270

Lys Glu Asp Gly His Thr Gln Lys Asn Asp Gly Asp Gly Pro Lys Glu
        275                 280                 285

Asp Gly His Thr Gln Lys Asn Asp Gly Asp Gly Pro Lys Glu Asp Gly
    290                 295                 300

His Thr Gln Lys Asn Asp Gly Asp Gly Pro Lys Glu Asp Gly His Thr
305                 310                 315                 320

Gln Lys Asn Asp Gly Asp Gly Pro Lys Glu Asp Gly His Thr Gln Lys
                325                 330                 335

Asn Asp Gly Asp Gly Pro Lys Glu Asp Gly His Thr Gln Lys Asn Asp
            340                 345                 350
```

```
Gly Asp Gly Pro Lys Glu Gly Glu Asn Leu Gln Gln Asn Asp Gly Asp
            355                 360                 365

Ala Gln Glu Lys Asn Glu Asp Gly His Asn Val Gly Asp Gly Ala Asn
370                 375                 380

Gly Asn Glu Asp Gly Asn Asp Asp Gln Pro Lys Glu His Ala Ala Gly
385                 390                 395                 400

Asn

<210> SEQ ID NO 20
<211> LENGTH: 3276
<212> TYPE: PRT
<213> ORGANISM: L. donovani

<400> SEQUENCE: 20

Met His Pro Ser Thr Val Arg Arg Glu Ala Glu Arg Val Lys Val Ser
1               5                   10                  15

Val Arg Val Arg Pro Leu Asn Glu Arg Glu Asn Asn Ala Pro Glu Gly
                20                  25                  30

Thr Lys Val Thr Val Ala Ala Lys Gln Ala Ala Ala Val Thr Val
            35                  40                  45

Lys Val Leu Gly Gly Ser Asn Asn Ser Gly Ala Ala Glu Ser Met Gly
50                  55                  60

Thr Ala Arg Arg Val Ala Gln Asp Phe Gln Phe Asp His Val Phe Trp
65                  70                  75                  80

Ser Val Glu Thr Pro Asp Ala Cys Gly Ala Thr Pro Ala Thr Gln Ala
                85                  90                  95

Asp Val Phe Arg Thr Ile Gly Tyr Pro Leu Val Gln His Ala Phe Asp
            100                 105                 110

Gly Phe Asn Ser Cys Leu Phe Ala Tyr Gly Gln Thr Gly Ser Gly Lys
        115                 120                 125

Thr Tyr Thr Met Met Gly Ala Asp Val Ser Val Leu Ser Gly Glu Gly
130                 135                 140

Asn Gly Val Thr Pro Arg Ile Cys Leu Glu Ile Phe Ala Arg Lys Ala
145                 150                 155                 160

Ser Val Glu Ala Gln Gly His Ser Arg Trp Ile Val Glu Leu Gly Tyr
                165                 170                 175

Val Glu Val Tyr Asn Glu Arg Val Ser Asp Leu Leu Gly Lys Arg Lys
            180                 185                 190

Lys Gly Val Lys Gly Gly Gly Glu Glu Val Tyr Val Asp Val Arg Glu
        195                 200                 205

His Pro Ser Arg Gly Val Phe Leu Glu Gly Gln Arg Leu Val Glu Val
210                 215                 220

Gly Ser Leu Asp Asp Val Arg Leu Ile Glu Ile Gly Asn Gly Val
225                 230                 235                 240

Arg His Thr Ala Ser Thr Lys Met Asn Asp Arg Ser Ser Arg Ser His
                245                 250                 255

Ala Ile Ile Met Leu Leu Leu Arg Glu Glu Arg Thr Met Thr Thr Lys
            260                 265                 270

Ser Gly Glu Thr Ile Arg Thr Ala Gly Lys Ser Ser Arg Met Asn Leu
        275                 280                 285

Val Asp Leu Ala Gly Ser Glu Arg Val Ala Gln Ser Gln Val Glu Gly
290                 295                 300

Gln Gln Phe Lys Glu Ala Thr His Ile Asn Leu Ser Leu Thr Thr Leu
305                 310                 315                 320
```

```
Gly Arg Val Ile Asp Val Leu Ala Asp Met Ala Thr Lys Gly Ala Lys
            325                 330                 335

Ala Gln Tyr Ser Val Ala Pro Phe Arg Asp Ser Lys Leu Thr Phe Ile
        340                 345                 350

Leu Lys Asp Ser Leu Gly Gly Asn Ser Lys Thr Phe Met Ile Ala Thr
    355                 360                 365

Val Ser Pro Ser Ala Leu Asn Tyr Glu Glu Thr Leu Ser Thr Leu Arg
370                 375                 380

Tyr Ala Ser Arg Ala Arg Asp Ile Val Asn Val Ala Gln Val Asn Glu
385                 390                 395                 400

Asp Pro Arg Ala Arg Ile Arg Glu Leu Glu Glu Gln Met Glu Asp
            405                 410                 415

Met Arg Gln Ala Met Ala Gly Gly Asp Pro Ala Tyr Val Ser Glu Leu
        420                 425                 430

Lys Lys Lys Leu Ala Leu Leu Glu Ser Glu Ala Gln Lys Arg Ala Ala
    435                 440                 445

Asp Leu Gln Ala Leu Glu Arg Glu Arg Glu His Asn Gln Val Gln Glu
450                 455                 460

Arg Leu Leu Arg Ala Thr Glu Ala Glu Lys Ser Glu Leu Glu Ser Arg
465                 470                 475                 480

Ala Ala Ala Leu Gln Glu Glu Met Ala Ala Thr Arg Arg Gln Ala Asp
            485                 490                 495

Lys Met Gln Ala Leu Asn Leu Arg Leu Lys Glu Gln Ala Arg Lys
        500                 505                 510

Glu Arg Glu Leu Leu Lys Glu Met Ala Lys Lys Asp Ala Ala Leu Ser
    515                 520                 525

Lys Val Arg Arg Lys Asp Ala Glu Ile Ala Ser Glu Arg Glu Lys
530                 535                 540

Leu Glu Ser Thr Val Ala Gln Leu Glu Arg Glu Gln Arg Glu Arg Glu
545                 550                 555                 560

Val Ala Leu Asp Ala Leu Gln Thr His Gln Arg Lys Leu Gln Glu Ala
            565                 570                 575

Leu Glu Ser Ser Glu Arg Thr Ala Ala Glu Arg Asp Gln Leu Leu Gln
        580                 585                 590

Gln Leu Thr Glu Leu Gln Ser Glu Arg Thr Gln Leu Ser Gln Val Val
    595                 600                 605

Thr Asp Arg Glu Arg Leu Thr Arg Asp Leu Gln Arg Ile Gln Tyr Glu
610                 615                 620

Tyr Gly Glu Thr Glu Leu Ala Arg Asp Val Ala Leu Cys Ala Ala Gln
625                 630                 635                 640

Glu Met Glu Ala Arg Tyr His Ala Ala Val Phe His Leu Gln Thr Leu
            645                 650                 655

Leu Glu Leu Ala Thr Glu Trp Glu Asp Ala Leu Arg Glu Arg Ala Leu
        660                 665                 670

Ala Glu Arg Asp Glu Ala Ala Ala Glu Leu Asp Ala Ala Ser
    675                 680                 685

Thr Ser Gln Asn Ala Arg Glu Ser Ala Ser Glu Arg Leu Thr Ser Leu
690                 695                 700

Glu Gln Leu Leu Arg Glu Ser Glu Glu Arg Ala Glu Leu Ala Ser
705                 710                 715                 720

Gln Leu Glu Ser Thr Thr Ala Ala Lys Met Ser Ala Glu Gln Asp Arg
            725                 730                 735

Glu Asn Thr Arg Ala Thr Leu Glu Gln Gln Leu Arg Asp Ser Glu Glu
```

-continued

```
                740                 745                 750
Arg Ala Ala Glu Leu Ala Ser Gln Leu Glu Ala Thr Ala Ala Lys
            755                 760                 765
Ser Ser Ala Glu Gln Asp Arg Glu Asn Thr Arg Ala Ala Leu Glu Gln
        770                 775                 780
Gln Leu Arg Asp Ser Glu Glu Arg Ala Ala Glu Leu Ala Ser Gln Leu
785                 790                 795                 800
Glu Ser Thr Thr Ala Ala Lys Thr Ser Ala Glu Gln Asp Arg Glu Asn
                805                 810                 815
Thr Arg Ala Thr Leu Glu Gln Gln Leu Arg Asp Ser Glu Glu Arg Ala
            820                 825                 830
Ala Glu Leu Ala Ser Gln Leu Glu Ser Thr Thr Ala Ala Lys Met Ser
            835                 840                 845
Ala Glu Gln Asp Arg Glu Asn Thr Arg Ala Ala Leu Glu Gln Gln Leu
            850                 855                 860
Leu Glu Ser Glu Glu Arg Ala Ala Glu Leu Lys Ala Glu Leu Glu Ala
865                 870                 875                 880
Thr Ala Ala Lys Ser Ser Ala Glu Gln Asp Arg Glu Asn Thr Arg
            885                 890                 895
Ala Ala Leu Glu Gln Gln Leu Arg Asp Ser Glu Glu Arg Ala Ala Glu
            900                 905                 910
Leu Ala Ser Gln Leu Glu Ser Thr Thr Ala Ala Lys Thr Ser Ala Glu
            915                 920                 925
Gln Asp Arg Glu Asn Thr Arg Ala Thr Leu Glu Gln Gln Leu Arg Asp
        930                 935                 940
Ser Glu Glu Arg Ala Ala Glu Leu Ala Ser Gln Leu Glu Ser Thr Thr
945                 950                 955                 960
Ala Ala Lys Met Ser Ala Glu Gln Asp Arg Glu Asn Thr Arg Ala Thr
            965                 970                 975
Leu Glu Gln Gln Leu Arg Asp Ser Glu Glu Arg Ala Ala Glu Leu Ala
            980                 985                 990
Ser Gln Leu Glu Ser Thr Thr Ala Ala Lys Met Ser Ala Glu Gln Asp
        995                 1000                1005
Arg Glu Asn Thr Arg Ala Thr Leu Glu Gln Gln Leu Arg Asp Ser
    1010                1015                1020
Glu Glu Arg Ala Ala Glu Leu Ala Ser Gln Leu Glu Ser Thr Thr
    1025                1030                1035
Ala Ala Lys Met Ser Ala Glu Gln Asp Arg Glu Asn Thr Arg Ala
    1040                1045                1050
Ala Leu Glu Gln Gln Leu Leu Glu Ser Glu Glu Arg Ala Ala Glu
    1055                1060                1065
Leu Lys Ala Glu Leu Glu Ala Thr Ala Ala Ala Lys Ser Ser Ala
    1070                1075                1080
Glu Gln Asp Arg Glu Asn Thr Arg Ala Thr Leu Glu Gln Gln Leu
    1085                1090                1095
Arg Asp Ser Glu Glu Arg Ala Ala Glu Leu Ala Ser Gln Leu Glu
    1100                1105                1110
Ala Thr Ala Ala Ala Lys Ser Ser Ala Glu Gln Asp Arg Glu Asn
    1115                1120                1125
Thr Arg Ala Ala Leu Glu Gln Gln Leu Arg Asp Ser Glu Glu Arg
    1130                1135                1140
Ala Gly Glu Leu Ala Ser Gln Leu Glu Ala Thr Ala Ala Ala Lys
    1145                1150                1155
```

```
Ser Ser Ala Glu Gln Asp Arg Glu Asn Thr Arg Ala Ala Leu Glu
1160                1165                1170

Gln Gln Leu Leu Glu Ser Glu Ala Arg Ala Ala Glu Leu Ala Ser
1175                1180                1185

Gln Leu Glu Ala Thr Ala Ala Ala Lys Ser Ser Ala Glu Gln Asp
1190                1195                1200

Arg Glu Asn Thr Arg Ala Ala Leu Glu Gln Gln Leu Arg Glu Ser
1205                1210                1215

Glu Ala Arg Ala Gly Glu Leu Ala Ser Gln Leu Glu Ala Thr Ala
1220                1225                1230

Ala Ala Lys Met Ser Ala Glu Gln Asp Arg Glu Asn Thr Arg Ala
1235                1240                1245

Ala Leu Glu Gln Gln Leu Arg Glu Ser Glu Glu Arg Ala Ala Glu
1250                1255                1260

Leu Ala Ser Gln Leu Glu Ala Thr Ala Ala Ala Lys Ser Ser Ala
1265                1270                1275

Glu Gln Asp Arg Glu Asn Thr Arg Ala Ala Leu Glu Gln Gln Leu
1280                1285                1290

Arg Glu Ser Glu Ala Arg Ala Ala Glu Leu Ala Ser Gln Leu Glu
1295                1300                1305

Ala Thr Ala Ala Ala Lys Ser Ser Ala Glu Gln Asp Arg Glu Asn
1310                1315                1320

Thr Arg Ala Ala Leu Glu Gln Gln Leu Arg Glu Ser Glu Ala Arg
1325                1330                1335

Ala Ala Glu Leu Ala Ser Gln Leu Glu Ala Thr Ala Ala Ala Lys
1340                1345                1350

Thr Ser Ala Glu Gln Asp Arg Glu Asn Thr Arg Ala Ala Leu Glu
1355                1360                1365

Gln Gln Leu Arg Glu Ser Glu Glu Arg Ala Ala Glu Leu Ala Ser
1370                1375                1380

Gln Leu Glu Ala Thr Ala Ala Ala Lys Met Ser Ala Glu Gln Asp
1385                1390                1395

Arg Glu Asn Thr Arg Ala Thr Leu Glu Gln Gln Leu Leu Glu Ser
1400                1405                1410

Glu Glu Arg Ala Ala Glu Leu Ala Ser Gln Leu Glu Ala Thr Ala
1415                1420                1425

Ala Ala Lys Met Ser Ala Glu Gln Asp Arg Glu Asn Thr Arg Ala
1430                1435                1440

Thr Leu Glu Gln Gln Leu Leu Glu Ser Glu Glu Arg Ala Ala Glu
1445                1450                1455

Leu Ala Ser Gln Leu Glu Ala Thr Ala Ala Ala Lys Ser Ser Ala
1460                1465                1470

Glu Gln Asp Arg Glu Asn Thr Arg Ala Ala Leu Glu Gln Gln Leu
1475                1480                1485

Arg Glu Ser Glu Ala Arg Ala Ala Glu Leu Ala Ser Gln Leu Glu
1490                1495                1500

Ala Thr Ala Ala Ala Lys Thr Ser Ala Glu Gln Asp Arg Glu Asn
1505                1510                1515

Thr Arg Ala Thr Leu Glu Gln Gln Leu Arg Glu Ser Glu Ala Arg
1520                1525                1530

Ala Gly Glu Leu Ala Ser Gln Leu Glu Ala Thr Ala Ala Ala Lys
1535                1540                1545
```

-continued

Ser Ser Ala Glu Gln Asp Arg Glu Asn Thr Arg Ala Ala Leu Glu
1550                1555                1560

Gln Gln Leu Arg Glu Ser Glu Arg Ala Ala Glu Leu Met Arg
    1565                1570                1575

Lys Leu Glu Ala Thr Ala Ala Lys Ser Ser Val Glu Gln Asp
    1580                1585                1590

Arg Glu Ser Met Lys Val Ala Leu Glu Ala Arg Thr Ala Glu Leu
1595                1600                1605

Ala Ser Arg Leu Lys Ala Thr Ala Ala Lys Thr Ser Ala Glu
1610                1615                1620

Gln Glu Arg Asp Arg Thr Arg Ala Thr Phe Glu Glu Arg Leu Arg
1625                1630                1635

Val Ala Glu Val Arg Ala Val Gln Leu Ala Ser Gln Leu Glu Ala
1640                1645                1650

Thr Ala Ala Ala Lys Ser Ser Val Glu Gln Asp Arg Glu Lys Thr
1655                1660                1665

Arg Thr Ala Leu Glu Ala Arg Val Ala Glu Leu Ala Ser Lys Leu
1670                1675                1680

Glu Ala Thr Ala Ala Ala Lys Ala Leu Val Glu Gln Asp Arg Glu
1685                1690                1695

Asn Thr Arg Ala Thr Leu Glu Glu Arg Leu Arg Val Ala Glu Val
1700                1705                1710

Arg Ala Ala Glu Leu Ala Ala Gln Leu Glu Ala Thr Ala Ala Ala
1715                1720                1725

Lys Ser Ser Val Glu Gln Asp Arg Glu Lys Thr Arg Thr Ala Leu
1730                1735                1740

Glu Ala Arg Val Ala Glu Leu Ala Ser Lys Leu Glu Ala Thr Ala
1745                1750                1755

Ala Ala Lys Thr Ser Ala Glu Gln Asp Arg Glu Ser Thr Arg Ala
1760                1765                1770

Thr Leu Lys Glu Arg Leu Arg Ile Ala Glu Val Arg Ala Ala Glu
1775                1780                1785

Leu Ala Thr Gln Leu Glu Ala Thr Ser Ala Ala Lys Thr Ser Val
1790                1795                1800

Glu Gln Asp Arg Glu Arg Thr Arg Ala Ala Leu Glu Ala Arg Val
1805                1810                1815

Ala Glu Leu Ala Ser Lys Leu Glu Ser Thr Ala Ala Ala Lys Ala
1820                1825                1830

Leu Val Glu Gln Asp Arg Glu Ser Thr Arg Ala Thr Leu Glu Glu
1835                1840                1845

Arg Leu Arg Ile Ala Glu Ala Arg Ala Ala Glu Leu Ala Ile Glu
1850                1855                1860

Leu Asp Ala Thr Ala Ala Ala Lys Ala Ser Met Glu His Asp Arg
1865                1870                1875

Glu Ser Thr Arg Ala Thr Leu Glu Glu Arg Leu Arg Ile Ala Glu
1880                1885                1890

Val Arg Gly Ala Glu Leu Ala Ser Gln Leu Glu Ala Thr Ala Ala
1895                1900                1905

Ala Lys Ala Leu Leu Glu Gln Asp Arg Glu Arg Thr Arg Ala Ala
1910                1915                1920

Leu Glu Ala Arg Ala Ala Glu Leu Ala Ser Lys Leu Glu Ala Thr
1925                1930                1935

Ala Ala Ala Lys Met Ser Ala Glu Gln Asp Arg Glu Arg Thr Arg

```
                     1940                1945                1950

Ala Ala Ile Glu Glu Gln Leu Arg Leu Ala Glu Val Arg Ala Ala
        1955                1960                1965

Glu Leu Ala Ser Gln Leu Glu Ala Thr Ala Ala Lys Ala Leu
    1970                1975                1980

Leu Glu Gln Asp Arg Glu Arg Thr Arg Ala Ala Leu Glu Gly Arg
        1985                1990                1995

Ala Ala Glu Leu Ala Arg Lys Leu Glu Ala Thr Ala Ile Ala Lys
        2000                2005                2010

Thr Ala Val Glu Gln Asp Arg Glu Ser Thr Arg Ala Thr Leu Glu
        2015                2020                2025

Glu Arg Leu Arg Gly Ala Glu Val Arg Val Ala Glu Leu Ala Ser
        2030                2035                2040

Gln Leu Glu Ala Thr Ala Ala Ala Lys Thr Ser Ala Glu Gln Glu
        2045                2050                2055

Arg Ala Asn Thr Arg Ala Ala Leu Glu Ala Arg Ala Ala Glu Leu
        2060                2065                2070

Ala Ser Lys Leu Glu Ala Thr Ala Ala Ala Lys Phe Ala Val Glu
        2075                2080                2085

Gln Asp Arg Glu Arg Thr Arg Ala Thr Leu Glu Glu Arg Leu Arg
        2090                2095                2100

Gly Ala Glu Val Arg Ala Ala Glu Leu Ala Arg Lys Leu Glu Ala
        2105                2110                2115

Thr Ala Ala Ala Lys Ala Ser Met Glu His Asp Arg Glu Ser Thr
        2120                2125                2130

Arg Ala Ala Leu Glu Glu Arg Leu Arg Gly Ala Glu Val Arg Ala
        2135                2140                2145

Ala Glu Leu Ala Ser Lys Leu Glu Ala Thr Ala Ala Ala Lys Ala
        2150                2155                2160

Ala Val Glu Gln Asp Arg Glu Arg Thr Arg Ala Thr Phe Glu Lys
        2165                2170                2175

Gln Leu Arg Asp Ser Glu Ala Arg Val Ala Glu Leu Ser Gly Gln
        2180                2185                2190

Leu Glu Ala Thr Ala Ala Ala Lys Thr Ser Ala Glu Gln Asp Arg
        2195                2200                2205

Glu Asn Thr Lys Ala Ala Leu Gln Ala Arg Ala Ala Glu Leu Lys
        2210                2215                2220

Ala Gln Leu Glu Ser Thr Ala Ala Ala Lys Met Ser Ala Glu Gln
        2225                2230                2235

Asp Arg Glu Asn Thr Arg Ala Ala Leu Glu Gln Arg Leu Arg Glu
        2240                2245                2250

Ser Glu Glu His Ala Ala Glu Leu Lys Ala Gln Leu Glu Ser Thr
        2255                2260                2265

Ala Ala Ala Lys Thr Ser Ala Asp Gln Asp Arg Glu Arg Met Arg
        2270                2275                2280

Val Ala Leu Gln Glu Arg Leu Arg Val Ala Glu Leu Arg Ala Ala
        2285                2290                2295

Glu Leu Ala Ser Gln Leu Glu Ala Thr Val Ala Ala Lys Thr Ser
        2300                2305                2310

Ala Glu Gln Asp Arg Glu Asn Thr Arg Ala Thr Leu Glu Gln Gln
        2315                2320                2325

Leu Arg Glu Ser Glu Ala Arg Ala Ala Glu Leu Ala Ser Gln Leu
        2330                2335                2340
```

```
Glu Ala Thr Ala Ala Ala Lys Ser Ser Ala Glu Gln Asp Arg Glu
        2345                2350                2355

Asn Thr Lys Ala Ala Leu Gln Ala Arg Ala Ala Glu Leu Ala Ser
    2360                2365                2370

Gln Leu Glu Ser Thr Ala Ala Ala Lys Met Ser Ala Glu Gln Asp
    2375                2380                2385

Arg Glu Asn Thr Arg Ala Thr Leu Glu Gln Gln Leu Arg Glu Ser
    2390                2395                2400

Glu Ala Arg Ala Ala Glu Leu Ala Ser Gln Leu Glu Ser Thr Ala
    2405                2410                2415

Ala Ala Lys Thr Ser Ala Glu Gln Asp Arg Glu Asn Thr Arg Ala
    2420                2425                2430

Thr Leu Glu Gln Gln Leu Arg Glu Ser Glu Ala Arg Ala Ala Glu
    2435                2440                2445

Leu Ala Ser Gln Leu Glu Ala Thr Ala Ala Ala Lys Ser Ser Ala
    2450                2455                2460

Glu Gln Asp Arg Glu Asn Thr Lys Ala Ala Leu Gln Ala Arg Ala
    2465                2470                2475

Ala Glu Leu Ala Ser Gln Leu Glu Ser Thr Ala Ala Ala Lys Met
    2480                2485                2490

Ser Ala Glu Gln Asp Arg Glu Asn Thr Arg Ala Ala Leu Glu Gln
    2495                2500                2505

Arg Leu Arg Glu Ser Glu Glu His Ala Ala Glu Leu Ala Ser Gln
    2510                2515                2520

Leu Glu Ala Thr Ala Ala Ala Lys Ser Ser Ala Glu Gln Asp Arg
    2525                2530                2535

Glu Asn Thr Arg Ala Thr Leu Glu Gln Gln Leu Arg Asp Ser Glu
    2540                2545                2550

Thr Arg Ala Ala Glu Leu Ala Ser Gln Leu Glu Ser Thr Ala Ala
    2555                2560                2565

Ala Lys Thr Ser Ala Glu Gln Asp Arg Glu Asn Thr Arg Ala Ala
    2570                2575                2580

Leu Glu Gln Arg Leu Arg Glu Ser Glu Ala Arg Ala Ala Glu Leu
    2585                2590                2595

Lys Ala Glu Leu Glu Ala Thr Ala Ala Ala Lys Thr Ser Ala Glu
    2600                2605                2610

Gln Asp Arg Glu Asn Thr Arg Ala Ala Leu Glu Gln Arg Leu Arg
    2615                2620                2625

Glu Ser Glu Ala Arg Ala Gly Glu Leu Lys Ala Glu Leu Glu Ala
    2630                2635                2640

Thr Thr Ala Ala Lys Thr Ser Ala Glu Gln Asp Arg Glu Asn Thr
    2645                2650                2655

Arg Ala Thr Leu Glu Gln Gln Leu Arg Asp Ser Glu Glu Arg Ala
    2660                2665                2670

Ala Glu Leu Ala Ser Gln Leu Glu Ala Thr Ala Ala Ala Lys Ser
    2675                2680                2685

Ser Ala Glu Gln Asp Arg Glu Asn Thr Arg Ala Thr Leu Glu Gln
    2690                2695                2700

Gln Leu Arg Glu Ser Glu Ala Arg Ala Gly Glu Leu Ala Ser Gln
    2705                2710                2715

Leu Glu Ala Thr Ala Ala Ala Lys Ser Ser Ala Glu Gln Asp Arg
    2720                2725                2730
```

```
Glu Asn Thr Arg Ala Ala Leu Gln Ala Arg Ala Glu Leu Lys
    2735                2740            2745
Ala Glu Leu Glu Ala Thr Ala Ala Ala Lys Thr Ser Ala Glu Gln
    2750                2755            2760
Asp Arg Glu Arg Met Arg Val Thr Leu Glu Glu Arg Leu Arg Val
    2765                2770            2775
Ala Glu Leu Arg Ala Ala Glu Leu Thr Gly Val Leu Glu Ala Thr
    2780                2785            2790
Ala Ala Ala Lys Thr Ser Ala Glu Gln Asp Arg Glu Arg Thr Arg
    2795                2800            2805
Thr Thr Leu Gln Glu Gln Leu Arg Glu Ser Glu Ala Arg Ala Ala
    2810                2815            2820
Glu Leu Lys Ala Glu Leu Glu Ala Thr Ala Ala Lys Ser Ser
    2825                2830            2835
Ala Glu Gln Asp Arg Glu Asn Thr Arg Ala Ala Leu Glu Glu Lys
    2840                2845            2850
Leu Arg Gly Thr Glu Ala Arg Ala Ala Glu Leu Glu Ala Arg Leu
    2855                2860            2865
Lys Ala Ile Ala Ala Thr Lys Ala Ser Ile Glu Gln Glu Arg Glu
    2870                2875            2880
Ser Ser Arg Ala Ser Leu Glu Glu Arg Leu Arg Gly Ser Glu Ala
    2885                2890            2895
Arg Ala Ala Glu Leu Ala Ala Arg Leu Lys Ala Ala Ala Ala Ala
    2900                2905            2910
Lys Thr Ser Ala Glu Gln Glu Arg Glu Asn Thr Arg Val Thr Leu
    2915                2920            2925
Glu Gln Gln Leu Arg Glu Ser Glu Lys Arg Ala Ala Glu Leu Ala
    2930                2935            2940
Ser Gln Leu Glu Ser Thr Ala Ala Ala Lys Thr Ser Ala Glu Gln
    2945                2950            2955
Asp Arg Glu Asn Thr Arg Val Thr Leu Gly Gln Gln Leu Arg Glu
    2960                2965            2970
Ser Glu Ala Arg Ala Ala Glu Leu Lys Ala Glu Leu Glu Ala Ala
    2975                2980            2985
Ala Ala Ala Lys Ser Ser Ala Glu Gln Asp Arg Glu Asn Thr Arg
    2990                2995            3000
Ala Ala Leu Glu Glu Lys Leu Arg Gly Thr Glu Ala Arg Ala Ala
    3005                3010            3015
Glu Leu Ala Ala Arg Leu Lys Ala Ile Ala Ala Met Lys Ala Ser
    3020                3025            3030
Met Val Gln Glu Arg Glu Ser Ala Arg Asp Ala Leu Glu Glu Lys
    3035                3040            3045
Leu Arg Gly Ser Glu Ala Arg Ala Ala Glu Leu Ala Ala Arg Leu
    3050                3055            3060
Lys Ala Ala Ala Ala Ala Lys Thr Ser Ala Glu Gln Glu Arg Glu
    3065                3070            3075
Asn Thr Arg Val Thr Leu Glu Gln Gln Leu Arg Glu Ser Glu Glu
    3080                3085            3090
Arg Ala Ala Glu Leu Ala Ser Gln Leu Glu Ala Ala Ala Ala Ala
    3095                3100            3105
Lys Ser Ser Ala Glu Gln Asp Arg Glu Asn Thr Arg Ala Ala Leu
    3110                3115            3120
Glu Glu Lys Leu Arg Asp Ser Glu Glu Arg Ala Ala Glu Leu Gly
```

-continued

```
                    3125                    3130                    3135

Thr Arg Val Lys Ala Ser Ser Ala Ala Lys Ala Leu Ala Glu Gln
    3140                    3145                    3150

Glu Arg Asp Arg Ile Arg Ala Ala Leu Glu Glu Lys Leu Arg Asp
    3155                    3160                    3165

Ser Glu Ala Arg Ala Ala Glu Leu Thr Thr Lys Leu Glu Ala Thr
    3170                    3175                    3180

Val Ala Ala Lys Ser Ser Ala Glu Gln Glu Arg Glu Asn Ile Lys
    3185                    3190                    3195

Val Ala Leu Glu Glu Glu Leu Val Asp Ala Arg Ala Lys Leu Ala
    3200                    3205                    3210

Gly Met Glu Ala Ser Leu Lys Glu Ser Lys Leu Glu Phe Glu Gly
    3215                    3220                    3225

Arg Val Gly Glu Leu Glu Gly Glu Cys Glu Lys Leu Arg Asn Asp
    3230                    3235                    3240

Lys Val Arg Tyr Ala Lys Lys Val Gln Ser Leu Glu Tyr Gln Met
    3245                    3250                    3255

Arg Ile Asp Glu Ala Arg Leu Lys Ala Arg Arg Asp Ala Val His
    3260                    3265                    3270

Arg Lys Glu
    3275

<210> SEQ ID NO 21
<211> LENGTH: 9
<212> TYPE: PRT
<213> ORGANISM: unknown
<220> FEATURE:
<223> OTHER INFORMATION: N-terminal sequence of fusion polypeptide

<400> SEQUENCE: 21

Met His His His His His His Thr Ser
1               5
```